US009052289B2

(12) United States Patent
Lawrence et al.

(10) Patent No.: US 9,052,289 B2
(45) Date of Patent: Jun. 9, 2015

(54) HYDROGEN SULFIDE ($H_2S$) DETECTION USING FUNCTIONALIZED NANOPARTICLES

(75) Inventors: Jimmy Lawrence, Cambridge, MA (US); Ronald van Hal, Watertown, MA (US); Jane Lam, Randolph, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 342 days.

(21) Appl. No.: 12/966,451

(22) Filed: Dec. 13, 2010

(65) Prior Publication Data
US 2012/0149117 A1 Jun. 14, 2012

(51) Int. Cl.
*G01N 33/24* (2006.01)
*G01N 33/22* (2006.01)
(Continued)

(52) U.S. Cl.
CPC ........... *G01N 21/643* (2013.01); *Y10T 436/184* (2015.01); *G01N 21/31* (2013.01); *G01N 33/004* (2013.01); *C09K 8/532* (2013.01); *C09K 2208/20* (2013.01)

(58) Field of Classification Search
CPC . G01N 21/643; G01N 21/31; G01N 33/0044; C09K 8/532; C09K 2208/20; Y10T 436/184
USPC ..................... 436/25, 28, 119–121, 164, 172; 422/82.09
See application file for complete search history.

(56) References Cited

U.S. PATENT DOCUMENTS 1,512,893 A * 10/1924 Fulweiler ...................... 436/121
2,413,261 A * 12/1946 Stackhouse .................... 436/52
(Continued)

FOREIGN PATENT DOCUMENTS

EP 0193369 9/1986
JP 61099849 5/1986
(Continued)

OTHER PUBLICATIONS

Askari et al., "A New Colloidal Technique for the Synthesis of Lead Sulfide Nanoparticles," Scientia Ironica, Jul. 2003, vol. 10(3): pp. 357-360.
(Continued)

*Primary Examiner* — Arlen Soderquist
(74) *Attorney, Agent, or Firm* — Daniel S. Matthews; Jakub Michna

(57) ABSTRACT

Methods and related apparatuses and mixtures are described for spectroscopic detection of hydrogen sulfide in a fluid, for example a formation fluid downhole. A reagent mixture is combined with the fluid. The reagent mixture includes metal ions for reacting with hydrogen sulfide forming a metal sulfide, and a capping agent that limits growth of the insoluble metal sulfide species by electrosteric or steric stabilization. The particle growth is one of chemical reaction or significant aggregation, and the capping agent further functionalizes the reagent mixture to exhibit properties outside the natural characteristics of the metal sulfide species to allow for spectroscopic detection of the metal sulfide species. The combined mixture and fluid is then spectroscopically interrogated to detect the presence of the metal sulfide thereby indicating the presence of hydrogen sulfide in the fluid. The mixture also includes chelating ligands for sustaining thermal endurance of the mixture under downhole conditions.

33 Claims, 17 Drawing Sheets

(51) Int. Cl.
*G01N 33/18* (2006.01)
*G01N 21/64* (2006.01)
*G01N 21/31* (2006.01)
*G01N 33/00* (2006.01)
*C09K 8/532* (2006.01)

(56) References Cited

U.S. PATENT DOCUMENTS

| | | | |
|---|---|---|---|
| 3,068,065 A * | 12/1962 | Hartley et al. | 423/228 |
| 3,660,035 A * | 5/1972 | Marsh | 436/60 |
| 3,702,235 A * | 11/1972 | Fallgatter | 436/121 |
| 3,740,187 A * | 6/1973 | Kowalski | 8/111 |
| 3,859,851 A | 1/1975 | Urbanosky | |
| 3,887,333 A * | 6/1975 | Mimura et al. | 436/34 |
| 3,919,056 A * | 11/1975 | Habulak | 205/310 |
| 3,976,812 A * | 8/1976 | Natale et al. | 427/74 |
| 4,026,667 A * | 5/1977 | Logan | 436/120 |
| 4,043,820 A * | 8/1977 | Landau | 106/31.18 |
| 4,102,861 A | 7/1978 | Wedel et al. | |
| 4,124,475 A * | 11/1978 | Zetter et al. | 204/406 |
| 4,133,908 A * | 1/1979 | Madsen | 430/413 |
| 4,158,074 A * | 6/1979 | Uchiyama et al. | 427/214 |
| 4,180,473 A * | 12/1979 | Maurer et al. | 514/499 |
| 4,211,532 A * | 7/1980 | Tobari et al. | 436/22 |
| 4,243,638 A * | 1/1981 | Jackovitz et al. | 423/17 |
| 4,252,655 A | 2/1981 | Carney | |
| 4,279,773 A * | 7/1981 | Franey et al. | 436/121 |
| 4,339,349 A | 7/1982 | Martin et al. | |
| 4,601,898 A * | 7/1986 | Stier et al. | 424/52 |
| 4,622,212 A * | 11/1986 | McManus et al. | 423/226 |
| 4,665,015 A * | 5/1987 | Iijima et al. | 430/558 |
| 4,707,271 A * | 11/1987 | Amjad et al. | 210/701 |
| 4,732,213 A | 3/1988 | Bennett et al. | |
| 4,737,491 A * | 4/1988 | Leppavuori et al. | 424/78.18 |
| 4,816,238 A * | 3/1989 | Jeffrey | 423/226 |
| 4,842,994 A * | 6/1989 | Sakanoue et al. | 430/543 |
| 4,860,581 A | 8/1989 | Zimmermann et al. | |
| 4,952,513 A * | 8/1990 | Koocher | 436/36 |
| 4,994,671 A | 2/1991 | Safinya et al. | |
| 5,061,566 A * | 10/1991 | Morgan | 428/423.1 |
| 5,143,716 A * | 9/1992 | Unger | 424/9.35 |
| 5,212,099 A * | 5/1993 | Marcus | 436/172 |
| 5,238,788 A * | 8/1993 | Kajiwara et al. | 430/357 |
| 5,266,800 A | 11/1993 | Mullins | |
| 5,292,361 A * | 3/1994 | Otsuka et al. | 106/1.28 |
| 5,326,567 A * | 7/1994 | Capelli | 424/405 |
| 5,397,708 A | 3/1995 | Lessard et al. | |
| 5,492,673 A * | 2/1996 | Curtis et al. | 73/1.74 |
| 5,501,935 A * | 3/1996 | Patel et al. | 430/137.14 |
| 5,517,024 A | 5/1996 | Mullins et al. | |
| 5,529,841 A * | 6/1996 | Neihof | 428/328 |
| 5,536,441 A * | 7/1996 | Chapple et al. | 252/186.33 |
| 5,624,597 A * | 4/1997 | Buhl et al. | 252/182.11 |
| 5,698,171 A * | 12/1997 | Trauffer et al. | 423/220 |
| 5,730,873 A * | 3/1998 | Hapka et al. | 210/632 |
| 5,733,964 A | 3/1998 | Johnston et al. | |
| 5,753,513 A * | 5/1998 | Amisar | 436/96 |
| 5,762,141 A | 6/1998 | Hutchins et al. | |
| 5,855,873 A * | 1/1999 | Yam | 424/49 |
| 5,874,315 A * | 2/1999 | Kraft et al. | 436/176 |
| 5,877,134 A * | 3/1999 | Scheper et al. | 510/220 |
| 5,882,943 A * | 3/1999 | Aldeen | 436/178 |
| 5,939,717 A | 8/1999 | Mullins | |
| 5,957,203 A | 9/1999 | Hutchins et al. | |
| 5,965,615 A * | 10/1999 | Kalvinsh et al. | |
| 6,090,858 A * | 7/2000 | El-Sayed | 516/97 |
| 6,106,854 A * | 8/2000 | Belfer et al. | 424/405 |
| 6,174,658 B1 * | 1/2001 | Yamazaki | 430/517 |
| 6,187,268 B1 * | 2/2001 | Albarella et al. | 422/408 |
| 6,217,780 B1 * | 4/2001 | Denkewicz et al. | 210/764 |
| 6,223,822 B1 | 5/2001 | Jones | |
| 6,350,431 B1 | 2/2002 | Snow et al. | |
| 6,479,708 B1 | 11/2002 | Jacobson et al. | |
| 6,576,264 B1 | 6/2003 | Henriksen et al. | |
| 6,593,287 B1 * | 7/2003 | Jordan et al. | 510/475 |
| 6,610,129 B1 * | 8/2003 | Sader et al. | 106/31.27 |
| 6,722,434 B2 * | 4/2004 | Reddy et al. | 166/292 |
| 6,758,090 B2 | 7/2004 | Bostrom et al. | |
| 6,767,392 B2 * | 7/2004 | Hayashi et al. | 106/1.23 |
| 6,773,926 B1 * | 8/2004 | Freund et al. | 436/149 |
| 6,811,885 B1 * | 11/2004 | Andriessen et al. | 428/464 |
| 6,905,886 B2 * | 6/2005 | Sundaram et al. | 436/534 |
| 6,939,717 B2 | 9/2005 | Jiang et al. | |
| 6,974,583 B2 | 12/2005 | Potin et al. | |
| 6,988,547 B2 | 1/2006 | Goodwin et al. | |
| 6,995,360 B2 | 2/2006 | Jones et al. | |
| 7,025,138 B2 | 4/2006 | Kurkjian et al. | |
| 7,176,271 B2 | 2/2007 | Bruchmann | |
| 7,368,132 B2 * | 5/2008 | Rocha | 424/641 |
| 7,416,582 B2 * | 8/2008 | Hakka et al. | 95/232 |
| 7,427,504 B2 | 9/2008 | Torgersen et al. | |
| 7,511,819 B2 | 3/2009 | DiFoggio | |
| 7,516,654 B2 | 4/2009 | DiFoggio | |
| 7,523,648 B2 | 4/2009 | Zougari | |
| 7,541,600 B2 | 6/2009 | Neuhauser et al. | |
| 7,604,049 B2 | 10/2009 | Vaidya et al. | |
| 7,645,397 B2 | 1/2010 | Parce et al. | |
| 7,722,953 B2 | 5/2010 | Korgel et al. | |
| 7,767,260 B2 | 8/2010 | Peng et al. | |
| 7,776,425 B2 | 8/2010 | Kalkan et al. | |
| 7,803,423 B2 | 9/2010 | O'Brien et al. | |
| 7,814,782 B2 | 10/2010 | DiFoggio | |
| 7,937,223 B2 | 5/2011 | Ciglenec et al. | |
| 7,959,864 B2 * | 6/2011 | Jiang et al. | 422/68.1 |
| 8,032,303 B2 | 10/2011 | Fujisawa et al. | |
| 8,039,791 B2 | 10/2011 | Dong et al. | |
| 8,056,408 B2 | 11/2011 | Pop et al. | |
| 8,058,071 B2 | 11/2011 | Jiang et al. | |
| 8,068,226 B2 | 11/2011 | Csutak | |
| 8,082,780 B2 | 12/2011 | Vannuffelen et al. | |
| 8,165,817 B2 | 4/2012 | Betancourt et al. | |
| 8,379,207 B2 | 2/2013 | DiFoggio et al. | |
| 8,518,702 B2 | 8/2013 | Jiang et al. | |
| 2002/0141970 A1 * | 10/2002 | Pettit et al. | 424/85.1 |
| 2003/0087423 A1 * | 5/2003 | Haywood et al. | 435/270 |
| 2003/0134423 A1 | 7/2003 | Jiang et al. | |
| 2004/0056186 A1 | 3/2004 | Simonetti et al. | |
| 2004/0129874 A1 | 7/2004 | Torgensen et al. | |
| 2005/0160701 A1 * | 7/2005 | Stevens | 53/425 |
| 2005/0208142 A1 * | 9/2005 | Zheng et al. | 424/489 |
| 2005/0250666 A1 | 11/2005 | Gatlin et al. | |
| 2005/0269499 A1 | 12/2005 | Jones et al. | |
| 2006/0062926 A1 * | 3/2006 | Richardson et al. | 427/440 |
| 2006/0083850 A1 * | 4/2006 | Valverde et al. | 427/58 |
| 2006/0216510 A1 | 9/2006 | Denisyuk et al. | |
| 2007/0015288 A1 * | 1/2007 | Hulteen et al. | 436/165 |
| 2007/0293611 A1 | 12/2007 | Ramanathan et al. | |
| 2008/0111064 A1 | 5/2008 | Andrews et al. | |
| 2009/0018246 A1 | 1/2009 | Blank et al. | |
| 2009/0107667 A1 * | 4/2009 | Mullins et al. | 166/250.12 |
| 2009/0137054 A1 | 5/2009 | Hoagland et al. | |
| 2009/0192051 A1 | 7/2009 | Carman | |
| 2009/0197781 A1 | 8/2009 | Sunkara | |
| 2009/0277625 A1 | 11/2009 | Bai et al. | |
| 2009/0302221 A1 | 12/2009 | Tavernier et al. | |
| 2010/0059375 A1 | 3/2010 | Weiller et al. | |
| 2010/0147065 A1 | 6/2010 | Tan et al. | |
| 2010/0181472 A1 | 7/2010 | Csutak | |
| 2010/0193767 A1 | 8/2010 | Naasani et al. | |
| 2010/0203648 A1 | 8/2010 | Porter et al. | |
| 2010/0305332 A1 | 12/2010 | Woolard et al. | |
| 2011/0023594 A1 | 2/2011 | Pelletier et al. | |
| 2012/0137764 A1 | 6/2012 | Lawrence et al. | |
| 2012/0138364 A1 | 6/2012 | Leonard et al. | |
| 2012/0145400 A1 | 6/2012 | Harrison et al. | |
| 2012/0149117 A1 | 6/2012 | Lawrence et al. | |
| 2012/0149604 A1 | 6/2012 | Lawrence et al. | |
| 2012/0273203 A1 | 11/2012 | Lawrence et al. | |
| 2012/0276648 A1 * | 11/2012 | van Hal et al. | 436/119 |
| 2013/0056626 A1 | 3/2013 | Shen et al. | |
| 2013/0071934 A1 | 3/2013 | Indo et al. | |
| 2013/0075093 A1 | 3/2013 | van Hal et al. | |

(56) References Cited

U.S. PATENT DOCUMENTS

| 2013/0104642 | A1 | 5/2013 | Pelletier et al. |
| 2013/0118734 | A1 | 5/2013 | Csutak |
| 2013/0188169 | A1 | 7/2013 | Harrison et al. |

FOREIGN PATENT DOCUMENTS

| JP | 03221142 | 9/1991 |
| JP | 05004021 | 1/1993 |
| WO | 9524962 | 9/1995 |
| WO | 9900575 | 1/1999 |
| WO | 0109039 | 2/2001 |
| WO | 0163094 | 8/2001 |
| WO | 2005001241 | 1/2005 |
| WO | 2005039656 | 5/2005 |
| WO | 20070143474 | 12/2007 |
| WO | 2010085001 | 7/2010 |

OTHER PUBLICATIONS

Auvray et al., "Formamide, a water substitute XIV (1) waterless microemulsions 8. Structural analysis by X-ray scattering of CTAB aggregates in formamide and in the microemulsion system (formamide, CTAB, isooctane, 1-butanol)," colloid & Polymer Science, 1987: pp. 925-932.

Brus, "Electron-electron and electron-hole interactions in small semiconductor crystallites: The size dependence of the lowest excited electronic state," J. Chem. Phys., May 1984, vol. 80(9): pp. 4403-4409.

Burgess et al., "Formation Testing and Sampling Through Casing," Oilfield Review, Spring 2002: pp. 46-57.

Cardoso et al., "Fluorometric fiber optic drop sensor for atmospheric hydrogen sulfide," Talanta, 1997, vol. 44: pp. 1099-1106.

Choi et al., "Aptamer-Capped Nanocrystal Quantum Dots: A New Method for Label-Free Protein Detection," J. Am. Chem. Soc., 2006, vol. 128(49): pp. 15584-15585.

"LUDOX Colloidal Silica Product Information," Brochure, W.R. Grace & Co., 2000: pp. 1-19.

Deželić et al., "Electron Microscopy of Ludox Colloidal Silica," Colloid and Polymer Science, vol. 171, 1960: pp. 42-45.

Eroğlu et al., "Hydrogen sulfide determination by solid surface luminescence," Fresenius J Anal Chem, 1996, vol. 355: p. 667-671.

Hashem et al., "Successful Low Level Detection of H2S Using Wireline Formation Testers," SPWLA 48th Annual Logging Symposium, 2007: pp. 1-16.

Henglein, "Photochemistry of Colloidal Cadmium Sulfide. 2. Effects of Adsorbed Methyl Viologen and of colloidal Platinum," J. Phys. Chem, 1982, vol. 86: pp. 2291-2293.

Henglein, "Photo-Degradation and Fluorescence of Colloidal-Cadmium Sulfide in Aqueous Solution," Ber. Bunsenges, Phys. Chem. 1982, vol. 86: pp. 301-305.

Lawrence et al., "The degradation mechanism of sulfonated poly(arylene ether sulfone)s in an oxidative environment," Journal of Membrane Science, 2008, vol. 325: pp. 633-640.

Patel et al., "Synthesis, Optical Spectroscopy and Ultrafast Electron Dynamics of PbS Nanoparticles with Different Surface Capping," J. Phys. Chem. B, 2000, vol. 104: pp. 11598-11605.

"Material Safety Data Sheet Formamide MSDS," Science Lab.com, 2005, last updated 2008: pp. 1-7, <http://www.sciencelab.com/xMSDS-Formamide-9927348>.

Smits et al., "In-Situ Optical Fluid Analysis as an Aid to Wireline Formation Sampling," SPE Formation Evaluation, Jun. 1995: pp. 91-98.

Spaziani et al., "On-line Determination of Sulfide by the 'Methylene Blue Method' With Diode-laser-based Fluorescence Detection," Analyst, Dec. 1997, vol. 122: pp. 1555-1557.

Vance et al., "Reservoir Souring: Mechanisms and Prevention," Petroleum Microbiology, Ed. Ollivier et al., ASM Press: Washington, D.C., 2005: pp. 123-142.

Virji et al., "Direct Electrical Measurement of the Conversion of Metal Acetates to Metal Sulfides by Hydrogen Sulfide," Inorg. Chem. 2006, vol. 45(26): pp. 10467-10471.

Vogel, "Chapter 10: Colorimetric and Spectrophotometric Analysis," A Text-Book of Quantitative Inorganic Analysis Including Elementary Instrumental Analysis Third Edition, John Wiley and Sons Inc.: New York, 1961: pp. 738-837.

Vogel, "Chapter 11: Fluorimetric* Analysis," A Text-Book of Quantitative Inorganic Analysis Including Elementary Instrumental Analysis Third Edition, John Wiley and Sons Inc.: New York, 1961: pp. 838-846.

Vogel, "Chapter 12: Nephelometric and Turbidimetric Analysis," A Text-Book of Quantitative Inorganic Analysis Including Elementary Instrumental Analysis Third Edition, John Wiley and Sons Inc.: New York, 1961: pp. 847-853.

Wardencki, "Problems with the determination of environmental sulphur compounds by gas chromatography," Journal of Chromatography A, 1998, vol. 793: pp. 1-19.

Yang, "The thioglycerol catalyzed reaction of metal salts and elemental sulfur: A new approach for the preparation of nanocrystalline metal sulfides," Colloids and Surfaces A: Physicochem. Eng. Aspects, 2006, vol. 276: 192-196.

* cited by examiner

HYDROGEN SULFIDE (H₂S) DETECTION USING FUNCTIONALIZED NANOPARTICLES

CROSS REFERENCE TO RELATED APPLICATION(S)

This patent application is related to commonly owned U.S. patent applications: 1) U.S. patent application Ser. No. 13/311,546 titled "CHEMICAL SCAVENGER FOR DOWNHOLE CHEMICAL ANALYSIS" by Jimmy Lawrence et al.; 2) U.S. patent application Ser. No. 12/966,492 titled "A DOWNHOLE MIXING DEVICE FOR MIXING A FIRST FLUID WITH A SECOND FLUID" by Jimmy Lawrence et al.; and 4) U.S. patent application Ser. No. 12/966,464 titled "A METHOD FOR MIXING FLUIDS DOWNHOLE" by Jimmy Lawrence et al., all of which are incorporated by reference in their entirety herein.

FIELD

The disclosed subject matter is generally related to detection and sensing of properties of fluids, such as formation fluids. More particularly, this patent specification relates to spectroscopic detection of substances such as Hydrogen Sulfide using reagent mixtures having metal ions for reacting with the hydrogen sulfide that forms a metal sulfide, along with a capping agent that limits growth of the insoluble metal sulfide species by electrosteric or steric stabilization.

BACKGROUND

Hydrogen sulfide ($H_2S$) occurs extensively in a number of subsurface hydrocarbon reservoirs under anaerobic conditions. The presence of hydrogen sulfide is highly corrosive to casing, tubing, and other metallic and polymeric tools, an effect that is considerably accelerated by low pH and the presence of carbon dioxide. This has a significant impact on the overall hydrocarbon recovery processes, during which materials selection and corrosion control are of great importance. Additionally, $H_2S$ is hazardous to humans even at minute concentration levels (for example, about 100 ppm).

The $H_2S$ content of reservoir fluids can be determined from samples collected by fluid sampling tools such as wireline fluid sampling tools or other sampling tools. Fluid samples are usually collected in metal containers, which are able to maintain the pressures at which the samples were collected. However, a problem associated with sampling fluids containing hydrogen sulfide is partial loss of the gas by reaction of the metal components, particularly those made from iron-based metals. The hydrogen sulfide gas readily forms non-volatile and insoluble metal sulfides by reaction with many metals and metal oxides, and analysis of the fluid samples can therefore give an underestimate of the true sulfide content.

Moreover, determining $H_2S$ concentration in downhole has also been difficult especially at low concentrations due to $H_2S$ scavenging occurring during the time when the samples are taken and brought for analysis. Thus, it is critically important for oil companies to assess the sulfur content of the reservoir fluid before they make a large investment to the field development. However, detecting sulfur in the early stage of the exploration is not easy or straightforward. It is noted, $H_2S$ is almost always underestimated due to scavenging by a formation sampling tool and sampling bottle, as noted above. Detecting sulfur content in heavy crude compounds is done by elemental analysis in a laboratory. While scavenging is not generally an issue for sulfurs in heavy compounds, the long lead-time, at least a month, more often much longer, is not suited for quick decision making. Therefore, in-situ, real time gas detection, particularly hydrogen sulfide is important for downhole fluid analysis As a result, the in situ detection and measurement of hydrogen sulfide is widely regarded as a critical parameter needed for well completion and production strategies. Due to the high chemical reactivity of sulfide species, various detection strategies including spectroscopy, electrochemistry, chromatography and combinations thereof have been proposed. For example, see Wardencki, W. J. "Problems with the determination of environmental sulphur compounds by gas chromatography" Journal of Chromatography A, Vol 793, 1 (1998). U.S. Pat. No. 6,939,717B2 describes feasible electrochemical and optical methodologies and embodiments aimed at downhole detection of hydrogen sulfide.

SUMMARY

The present disclosed subject matter relates to a mixture that is provided for use in spectroscopic detection of hydrogen sulfide in a fluid, for example a formation fluid downhole. A reagent mixture is combined with the fluid. The reagent mixture includes metal ions for reacting with hydrogen sulfide forming a metal sulfide, and a capping agent that limits growth of the insoluble metal sulfide species by electrosteric or steric stabilization. For example, it limits the growth due to chemical reaction or due to aggregation and prevents precipitation. The particle growth is one of chemical reaction or significant aggregation, and the capping agent further functionalizes the reagent mixture to exhibit properties outside the natural characteristics of the metal sulfide species to allow for spectroscopic detection of the metal sulfide species. The combined mixture and fluid is then spectroscopically interrogated to detect the presence of the metal sulfide thereby indicating the presence of hydrogen sulfide in the fluid. It is possible the mixture may include chelating ligands for sustaining thermal endurance of the mixture under downhole conditions.

According to aspects of the subject matter disclosed, the solvent can be one of water, an organic polar solvent, an ionic liquid or some combination thereof. Further, the metal ions can be from a soft metal group consisting of cadmium, mercury, silver, gold, palladium, rhodium, ruthenium, osmium, iridium, platinum or thallium. Further still, the metal ions can be from the intermediate metal group consisting of manganese, iron, cobalt, nickel, copper, zinc, molybdenum, technetium, indium, tantalum, tungsten, rhenium, lead or bismuth. It is possible the capping agent can be a soluble polymer to allow for spectroscopic detection of the metal sulfide species that is under downhole conditions of sustain high temperatures at one of 100 deg Cs or at least 150 deg C. and more. Further, the capping agent can be a soluble polymer from the group consisting of one of a poly(acrylamide-co-acrylic acid), a poly(acrylic acid), a chitosan, a poly(vinyl pyridine), a poly(ethylene glycol) monolaurate, a poly(ethylene oxide), a poly(vinyl alcohol), a poly(4-styrene sulfonic acid), a poly (methacrylic acid) or a poly (vinyl pyrrolidone). It is noted that the capping agent can have an approximate concentration between 0 to 5 mass percent. Further, the capping agent is a alternative capping agent, a binder agent or a ligand agent that is from the group consisting of one of a thioglycerol, nitrilo triacetic acid (NTA), ethylenediaminetetraacetic acid (EDTA), sodium dodecyl sulfonate or sodium dodecyl benzene sulfonate.

According to aspects of the subject matter disclosed, the reagent mixture can further comprise a chelating ligand to sustain endurance at high temperatures under downhole conditions. It is possible that the chelating ligand can have a pK lower than a pH of the reagent mixture. Further, it is noted a ratio of the chelating ligand to the metal ion can be between about 0 to 2. Further, the reagent mixture can be functionalized to exhibit properties outside the natural characteristics of the metal sulfide species by one of improving spectroscopic detection such as optical properties and electrical properties and limits further aggregation and chemical reaction. Further still, the reagent mixture can further comprise of a radical scavenging agent to sustain endurance at high temperatures after reaction and to functionalize the reagent mixture to exhibit properties outside the natural characteristics of the metal sulfide species such as reducing a rate of degradation of the metal sulfide species. Wherein, the radical scavenging agent can be between about 0 to 5 volume percent. It is noted that the metal sulfide can be a nanoparticle kept in suspension by the capping agent to form a homogenous mixture.

In accordance with another embodiment of the disclosed subject matter, a reagent mixture for use in spectroscopic detection of hydrogen sulfide in a fluid. The homogenous reagent mixture includes metal ions dissolved in a solvent such as water for reacting with hydrogen sulfide thereby forming a metal sulfide species. A capping agent such as a poly(acrylic acid) (PAA) that limits growth of the insoluble metal sulfide species by electrosteric or steric stabilization. The particle growth is one of chemical reaction or significant aggregation, and the capping agent further functionalizes the reagent mixture to exhibit properties outside the natural characteristics of the metal sulfide species to allow for spectroscopic detection of the metal sulfide species. It is noted that the pH range of the poly(acrylic acid) (PAA) based reagent mixture is from approximately 2 to 5.

According to aspects of the subject matter disclosed, the metal ions can be bismuth. Further, the reagent mixture may further comprise of a radical scavenging agent such as ethylene glycol to sustain endurance at high temperatures after reaction as well as functionalizes the reagent mixture to exhibit properties outside the natural characteristics of a bismuth sulfide species such as reducing a rate of degradation of the bismuth sulfide species. It is possible that the metal ions are cadmium. Further, the reagent mixture may further comprise of a chelating ligand having a pK lower than the pH of the reagent mixture. Further still, the spectroscopy can be used for the detection of the hydrogen sulfide after the homogenous reagent mixture is exposed to hydrogen sulfide to form the metal sulfide species.

In accordance with another embodiment of the disclosed subject matter, a method of detecting hydrogen sulfide in a formation fluid. The method includes combining a reagent mixture with the formation fluid, wherein the reagent mixture includes metal ions such as bismuth or cadmium dissolved in a solvent for reacting with hydrogen sulfide. Thereby, forming a metal sulfide species, and a capping agent that limits growth of the insoluble metal sulfide species by electrosteric or steric stabilization, the particle growth is one of chemical reaction or significant aggregation. Wherein, the capping agent further functionalizes the reagent mixture to exhibit properties outside the natural characteristics of the metal sulfide species to allow for spectroscopic detection of the metal sulfide species. Finally, spectroscopically interrogating the combined homogenous reagent mixture and the formation fluid so as to detect the presence of one of an optical property or an electrical property of the metal sulfide thereby indicating the presence of hydrogen sulfide in the formation fluid.

According to aspects of the subject matter disclosed, the spectroscopy interrogating can include measuring the optical property such as one of an optical density of the metal sulfide species or a fluorescence of the metal sulfide species, so the quantity of hydrogen sulfide in the formation fluid is capable of being measured while under downhole conditions. Further, the spectroscopy interrogating includes measuring before mixing the optical property such as the optical density or the fluorescence of one of the reagent, the formation fluid or both. Further still, the combining can further comprise introducing the homogenous reagent mixture into a downhole flowline containing the formation fluid. It is possible, the spectroscopically interrogating can further comprise interrogating through an optical window in the flowline downstream from the location of introduction of the detection mixture. It is noted, the combining may further comprise introducing the formation fluid into a container containing the homogenous reagent mixture, and the interrogating further comprises interrogating through an optical window in a wall of the container while in a subterranean environment. It is also possible, the combining further comprises mechanically stirring the homogenous reagent mixture and the formation fluid in the container to shorten a rate of time used to carry out the interrogating. Further still, the combining may further comprise introducing the formation fluid into a container containing the homogenous reagent mixture. Introducing the combined homogenous reagent mixture and the formation fluid from the container into a downhole flowline, and spectroscopically interrogating through an optical window in a wall of the flowline.

According to aspects of the subject matter disclosed, the reagent mixture may further comprise a radical scavenging agent such as ethylene glycol to sustain endurance at high temperatures after reaction as well as functionalizes the homogenous reagent mixture to exhibit properties outside the natural characteristics of a bismuth sulfide species such as reducing a rate of degradation of the bismuth sulfide species. It is also possible, the reagent mixture can further comprise of adding chelating ligands to the homogenous reagent mixture for sustaining thermal endurance of the mixture under downhole conditions, wherein the metal ions are cadmium, and the spectroscopically interrogating is through an optical window in a wall of the flowline while in a subterranean environment.

In accordance with another embodiment of the disclosed subject matter, a method of detecting hydrogen sulfide in a formation fluid under downhole conditions at sustained temperatures of 150 deg C. The method includes exposing a reagent mixture with the formation fluid, wherein the reagent mixture includes metal ions such as bismuth or cadmium dissolved in a solvent for reacting with hydrogen sulfide. Thereby, forming a metal sulfide species, and a capping agent that limits growth of the insoluble metal sulfide species by electro-steric or steric stabilization, the particle growth is one of chemical reaction or significant aggregation. The capping agent further functionalizes the reagent mixture to exhibit properties outside the natural characteristics of the metal sulfide species to allow for spectroscopic detection of the metal sulfide species. Then, spectroscopically interrogating the exposed homogenous reagent mixture so as to detect the presence of one of an optical property or an electrical property of the metal sulfide thereby indicating the presence of hydrogen sulfide in the formation fluid.

In accordance with another embodiment of the disclosed subject matter, a system for detecting hydrogen sulfide in a fluid under downhole conditions. The system includes a reagent mixture having metal ions dissolved in a solvent such as water for reacting with hydrogen sulfide thereby forming a metal sulfide species. A capping agent that limits growth of the insoluble metal sulfide species by electrosteric or steric stabilization, wherein the particle growth is one of chemical reaction or significant aggregation. Wherein, the capping agent further functionalizes the reagent mixture to exhibit properties outside the natural characteristics of the metal sulfide species to allow for spectroscopic detection of the metal sulfide species. A downhole reagent mixture delivery system for exposing the reagent mixture to fluids collected from a subterranean formation in a downhole setting. Finally, an optical detection system for detecting the reacted homogenous mixture that indicated the presence of hydrogen sulfide in the exposed formation fluid.

According to aspects of the subject matter disclosed, the reagent mixture may the optical detection system uses spectroscopy detection to detect at least one optical property such as one of an optical density of the metal sulfide species or a fluorescence of the metal sulfide species. It is possible, the downhole reagent mixture delivery system includes a mixture reservoir and a valve system for introducing the reagent mixture into a flowline for carrying the subterranean fluids, and the optical detection system includes a light source, an interrogation window in the flowline and an optical detector.

In accordance with another embodiment of the disclosed subject matter, a method of dispersing a reagent mixture that is otherwise insoluble in a solvent into a homogeneous solution for spectroscopic detection of hydrogen sulfide of a formation fluid under downhole conditions having sustained temperatures of 100 deg C. or more. The method includes combining the reagent mixture having metal ions dissolved with the solvent with a capping agent. The reagent mixture having a pH range of approximately 2 to 5. A capping agent such as a poly (acrylic acid) limits growth of the insoluble metal sulfide species by electrosteric or steric stabilization. The particle growth is one of chemical reaction or significant aggregation, and the capping agent further functionalizes the reagent mixture to exhibit properties outside the natural characteristics of the metal sulfide species to allow for spectroscopic detection of the metal sulfide species.

Further features and advantages of the disclosed subject matter will become more readily apparent from the following detailed description when taken in conjunction with the accompanying Drawing.

BRIEF DESCRIPTION OF THE DRAWINGS

The present disclosed subject matter is further described in the detailed description which follows, in reference to the noted plurality of drawings by way of non-limiting examples of exemplary embodiments of the present disclosed subject matter, in which like reference numerals represent similar parts throughout the several views of the drawings, and wherein.

DETAILED DESCRIPTION OF THE PREFERRED EMBODIMENTS

Figure 1:
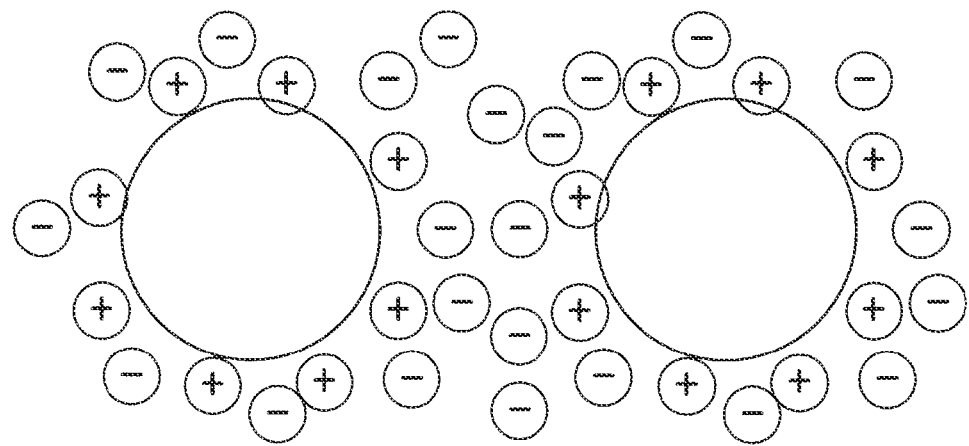
FIG. 1 shows a prior art schematic diagram of stabilized nanoparticles by electrostatic repulsion, according to the disclosed subject matter.

The particulars shown herein are by way of example and for purposes of illustrative discussion of the embodiments of the present disclosed subject matter only and are presented in the cause of providing what is believed to be the most useful and readily understood description of the principles and conceptual aspects of the present disclosed subject matter. In this regard, no attempt is made to show structural details of the present disclosed subject matter in more detail than is necessary for the fundamental understanding of the present disclosed subject matter, the description taken with the drawings making apparent to those skilled in the art how the several forms of the present disclosed subject matter may be embodied in practice. Further, like reference numbers and designations in the various drawings indicated like elements.

The present disclosed subject matter relates to a mixture that is provided for use in spectroscopic detection of hydrogen sulfide in a fluid, for example a formation fluid downhole. A reagent mixture is combined with the fluid. The reagent mixture includes metal ions for reacting with hydrogen sulfide forming a metal sulfide, and a capping agent that limits growth of the insoluble metal sulfide species by electrosteric or steric stabilization. The particle growth is one of chemical reaction or significant aggregation, and the capping agent further functionalizes the reagent mixture to exhibit properties outside the natural characteristics of the metal sulfide species to allow for spectroscopic detection of the metal sulfide species. The combined mixture and fluid is then spectroscopically interrogated to detect the presence of the metal sulfide thereby indicating the presence of hydrogen sulfide in the fluid. The mixture also includes chelating ligands for sustaining thermal endurance of the mixture under downhole conditions.

It has been found that a difficulty in hydrogen sulfide ($H_2S$) detection exits due to the rapid precipitation of the metal sulfides when the $H_2S$ reacts with metal ions. Since the metal sulfide very quickly precipitates out of the detection solution, its optical detection is often very difficult or impractical. In US 2009/0107667 the inventors try to solve this problem by using electrostatic stabilization with an overwhelming amount of silica nanoparticles in an alkaline aqueous medium. The metal sulfides are clustered on the surface of the silica nanoparticles preventing significant aggregation and precipitation of the metal sulfides. However, the electrostatic effect is highly sensitive to variations in the ionic strength and pH of the suspension. The electrostatic effect becomes less effective at small increases in the ion concentration. Furthermore, the silica suspension tends to form a gel when small amounts of water evaporate, when the ionic strength increases due to contact with salts or salt water and when the pH of the solution is changed by more than 2 pH units. These events are impossible to prevent under down hole conditions where the suspension is exposed to sour gases ($H_{2S}$ and $CO_2$), saline water and high temperatures. Gel formation in the flow line will cause the clogging of the flow line.

According to embodiments of the disclosed subject matter, it is noted that in order to detect and measure certain downhole gas compounds such as hydrogen sulfide (i.e., determining the sulfide concentration in a solution with metal salt solutions), one could use a functional surface capping agent to stabilize the metal sulfide nanoparticles formed from the reaction between the metal salt and sulfide. This metal sulfide nanoparticle can have distinctive properties (resistance, optical absorption, magnetic susceptibility) that may be used for quantifying sulfide content of downhole fluids. For example, the optical absorption value will increase when metal sulfide nanoparticles are formed in the solution.

The capping agent can work by steric or electrosteric stabilization. For example, neutral polymers like poly (vinyl alcohol) and poly (ethylene oxide) use steric stabilization whereas charged polymers like poly (acrylic acid) and poly (vinyl pyridine use electrosteric stabilization. The capping agent limits the growth of the metal sulfide particles as result of the reaction between the metal ions and the sulfide, prevents significant agglomeration of the metal sulfide nanoparticles and finally prevents precipitation.

Because of steric or electrosteric stabilization provided by the capping agent, the metal sulfide nanoparticle suspension is stable and can be tailored to withstand various pH condition and temperature higher than 100° C. This concept can be useful for many applications, such as downhole spectroscopy of hydrogen sulfide using downhole tool, by non-limiting example, Schlumberger's Modular Dynamics Tester (MDT). Moreover, surface capping agents such as functionalized polymers mentioned in this patent application are solvent soluble, thus the risk of clogging the flowline is significantly small. Various surface capping agent functionalized polymer and metal salt combinations available made this concept extensible towards various conditions or concentrations.

Various other methods to synthesize stable nanocrystals for quantum dot applications may be applicable regarding the stability and aggregation issue, but bring forth issues that cannot be overcome. The differences between quantum dot synthesis and the subject matter disclosed in this application, by non-limiting example, are that the products need to: 1) survive long exposure to high temperature while maintaining its stability; 2) provide an understanding as to how the reagents are reacted with sulfide relating to variables such as temperature, adding time, etc; provide an understanding as to the sulfide amount used in the reaction; 3) provide an understanding to the capping agents employed as to how they maintain stability at wide temperature range.

For example, a capping agent can be an absorbed monolayer of molecules (usually organic/inorganic molecules/ macromolecules, for instance single complex molecules, surfactants, polymers, etc) to stabilize nanoparticles solution. Nanoparticles capped with capping agents can be functionalized to exhibit new properties such as their optical and electrical properties, since capping agents enable the control of their size. For example, Further, the capping agent can also be used to protect the surface of nanoparticles, to prevent the particles from degrading, preserve its intrinsic properties, or to limit further growth due to agglomeration. For instance, capping agents like macromolecules such as polymers and dendrimers can protect nanoparticles from aggregation and further chemical reaction, among other things. Capping agents do not necessarily have to be a dissolved organic compound. Solvents such as N,N-dimethylformamide, dimethylsulfoxide, glycol based solvents, mercaptoalcohol and alkanoamines can also act as capping agent.

Nanoparticles prepared with different capping agents can have different sizes. For example, tin particles capped with hydrobenzamide, poly (vinyl pyrrolidone) and citrate have different particle size.

The capping mechanism can be briefly described here as a process where adsorbed and surrounding molecules attribute additional energy penalty that is bigger than the attractive van der Waals force between the particles, therefore preventing the particles to attract to each other and grow in size.

The standard laboratory techniques to measure sulfide concentration in samples are a lead-acetate tape analyzer or iodometric titration. The lead-acetate tape analyzer is expensive, requires regular calibration and is less suitable for water based samples. The iodometric is complex, labor intensive and thus prone to errors, has some cross-sensitivities and requires highest purity chemicals. The present disclosed subject matter involves a method that is extremely simple, cheap and less prone to errors. A small amount of water based sample is added to the reagent mixture, stirred and the optical absorbance is measured to obtain the sulfide concentration. Gas samples are injected in a closed vial, shaken, and optical absorbance is measured to obtain the sulfide concentration.

Figure 2:
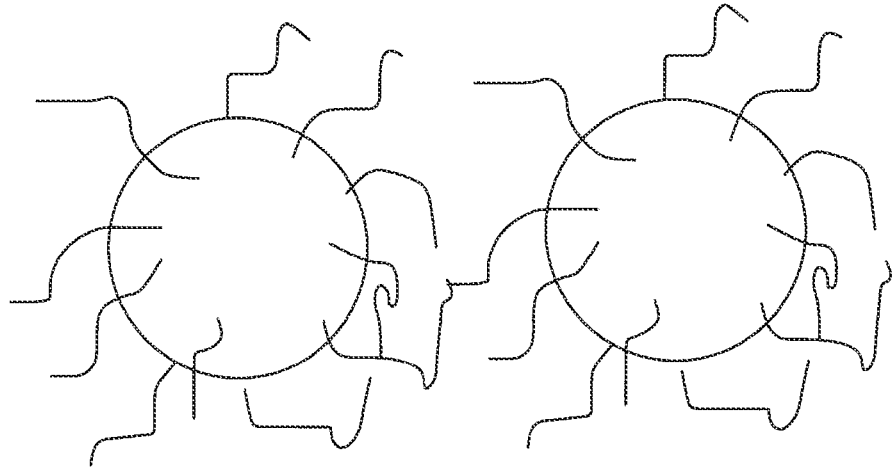
FIG. 2 shows a prior art schematic diagram of stabilized nanoparticles by steric barrier, according to the disclosed subject matter.
Figure 3:
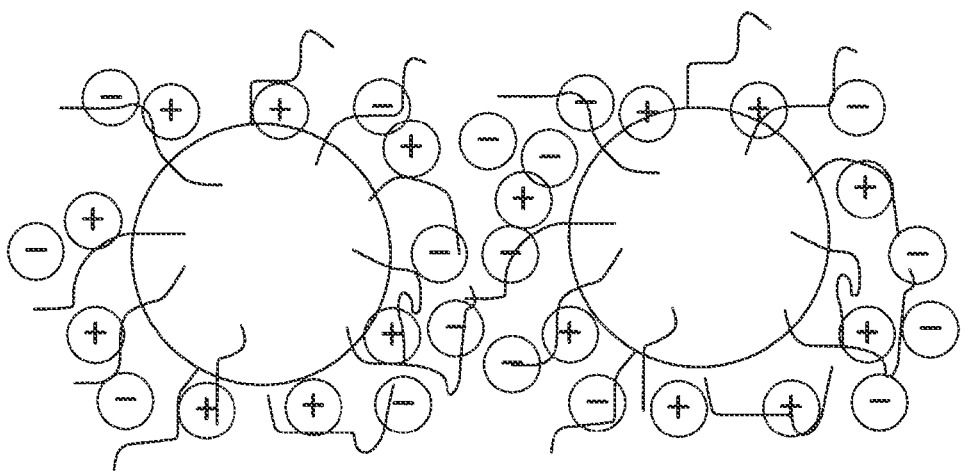
FIG. 3 shows a prior art schematic diagram of stabilized nanoparticles by electrosteric interactions, according to the disclosed subject matter.

FIG. 1 to FIG. 3 disclose the three main ways to stabilize nanocolloids, namely: FIG. 1 shows a prior art schematic diagram of stabilized nanoparticles by electrostatic repulsion; FIG. 2 shows a prior art schematic diagram of stabilized nanoparticles by steric barrier; and FIG. 3 shows a prior art schematic diagram of stabilized nanoparticles by electrosteric interactions. The extra penalty energy added by these methods is electrostatic repulsion of particles with similar charges, steric forces form physical and the combination of both electrostatic and steric forces, respectively. The subject matter disclosed focuses on steric and electrosteric stabilization (see FIGS. 2 and 3). In FIG. 1, the electrostatic stabilization is prone to change the electrical double layer thickness because of agitation, temperature change and ionic species.

Still referring to FIG. 1 to FIG. 3, adsorption of capping agents on the surface of nanoparticles will limit nanoparticles aggregation in its matrix due to steric forces or electro-steric forces, as long as the stabilization force is larger than Van der Waals force. Initially we tested poly (vinyl alcohol) as a capping agent to confirm the concept along with obtaining positive results.

Still referring to FIG. 1 to FIG. 3, in at least one aspect several ml of metal salt solution (typically resulting in a 1-5 mM solution) was mixed with approximately 2 wt % of polymer solutions which the solution was stirred for approximately 30 minutes to 1 hour vigorously.

Many studies were conducted for various combinations of reagent compounds. For example, regarding metal salts we used transition metal salt compounds. It is noted that are acetate, chloride, sulfate or nitrate salt form of copper, zinc, nickel, lead, cobalt, iron, cadmium, tin, bismuth, arsenic.

Still referring to FIG. 1 to FIG. 3, for polymer solutions as capping agents we used poly(acrylamide-co-acrylic acid), poly(acrylic acid), chitosan, poly(vinyl pyridine), poly(ethylene glycol) monolaurate, poly(ethylene oxide), poly(vinyl alcohol), poly(4-styrene sulfonic acid), poly (methacrylic acid), poly (vinyl pyrrolidone).

Further, as an alternative capping, binder and ligand agent, we used thioglycerol, nitrilo triacetic acid (NTA), ethylenediaminetetraacetic acid (EDTA), sodium dodecyl sulfonate and sodium dodecyl benzene sulfonate.

For solvents we used ethylene glycol, propylene glycol, diethylene glycol monobutyl ether, formamide, thioglycerol, N,N-dimethylformamide (DMF), tryoctyl phosphine oxide (TOPO), oleylamine, propylene carbonate, benzyl alcohol, diethanolamine (DEA), triethanolamine (TEA) and methyldiethanolamine (MDEA). For aqueous solution, it is noted that the pH is adjusted according to give stability, for example, especially for non-acidic polymer. It was also noticed that while most of the systems were stable at temperature up to 100° C., most of the combinations mentioned above showed coloration when heated at 150° C. It was also noted that cadmium-poly(acrylic acid)-water, bismuth-poly (acrylic acid)-water, cadmium-poly(acrylic acid)-diethylene glycol mono butyl ether, bismuth-poly(acrylic acid)-diethylene glycol mono butyl ether were relatively stable compared to other metal-polymer-solvent compounds when heated at 150° C., showing almost no color change within visible range.

Regarding studying the reaction with sulfide, we prepared several sample bottles of any of the solutions mentioned above and add $Na_2S$ or bubble $H_{2S}$ gas to test its reactivity with sulfide. At least one aspect used for better concentration adjustment, we typically use $Na_2S$ in range of 0-3 mM in the final solution, by non-limiting example.

Figure 4:
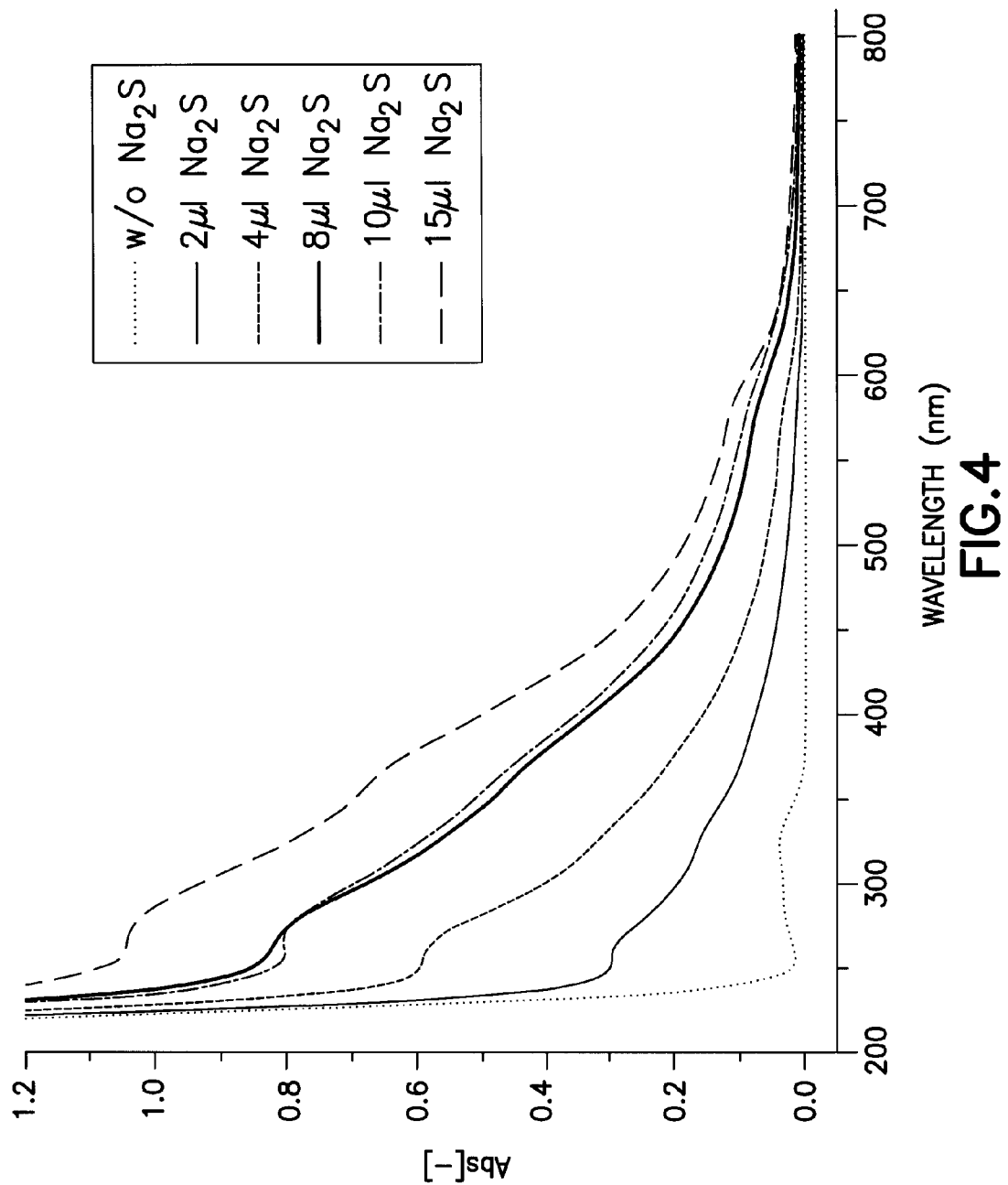
FIG. 4 shows the UV-Vis spectra of Pb-PVA solution at addition of various amounts of sulfide, according to embodiments of the disclosed subject matter.

FIG. 4 shows the UV-Vis spectra of Pb-PVA based solution upon an addition of sulfide. To get to the results of FIG. 4, a comparison of a solution before and after the addition of sulfide was conducted, it was noticed that the color change induced by sulfide addition was light yellow to brown, depending on the sulfide concentration. The formed solution was homogeneous, neither particle nor precipitation visible to eyes were observed.

Still referring to FIG. 4, each 1 ml of the solution was added with 2 µl, 4 µl, 8 µl and 15 µl of $Na_2S$ solution and their spectra were taken using 2 mm optical cell. Their UV-VIS spectra are shown in FIG. 4.

Figure 5A:
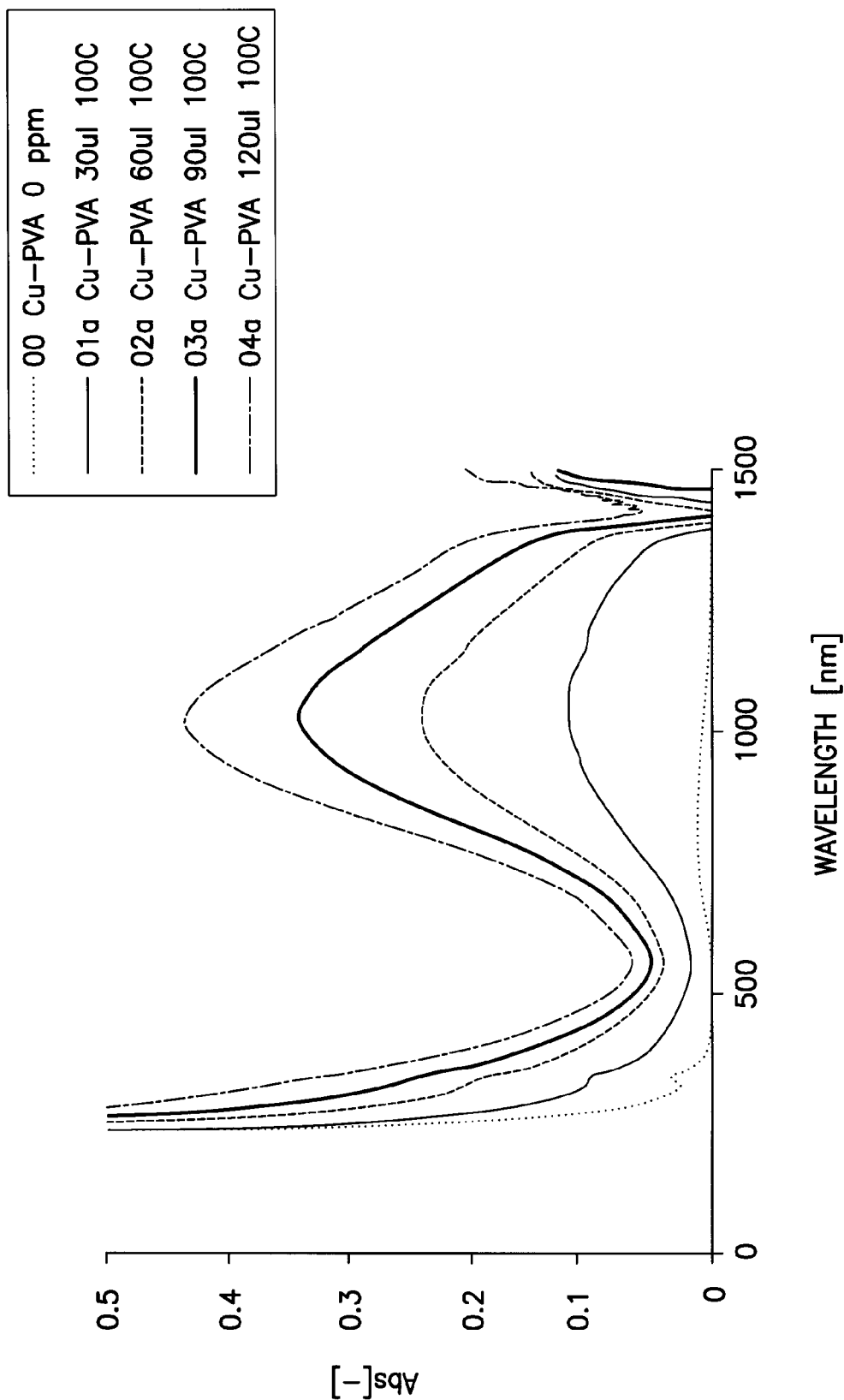
FIG. 5A shows the comparison of absorbance spectra of various amounts of sulfide added to Cu-PVA solution, according to embodiments of the disclosed subject matter.
Figure 5B:
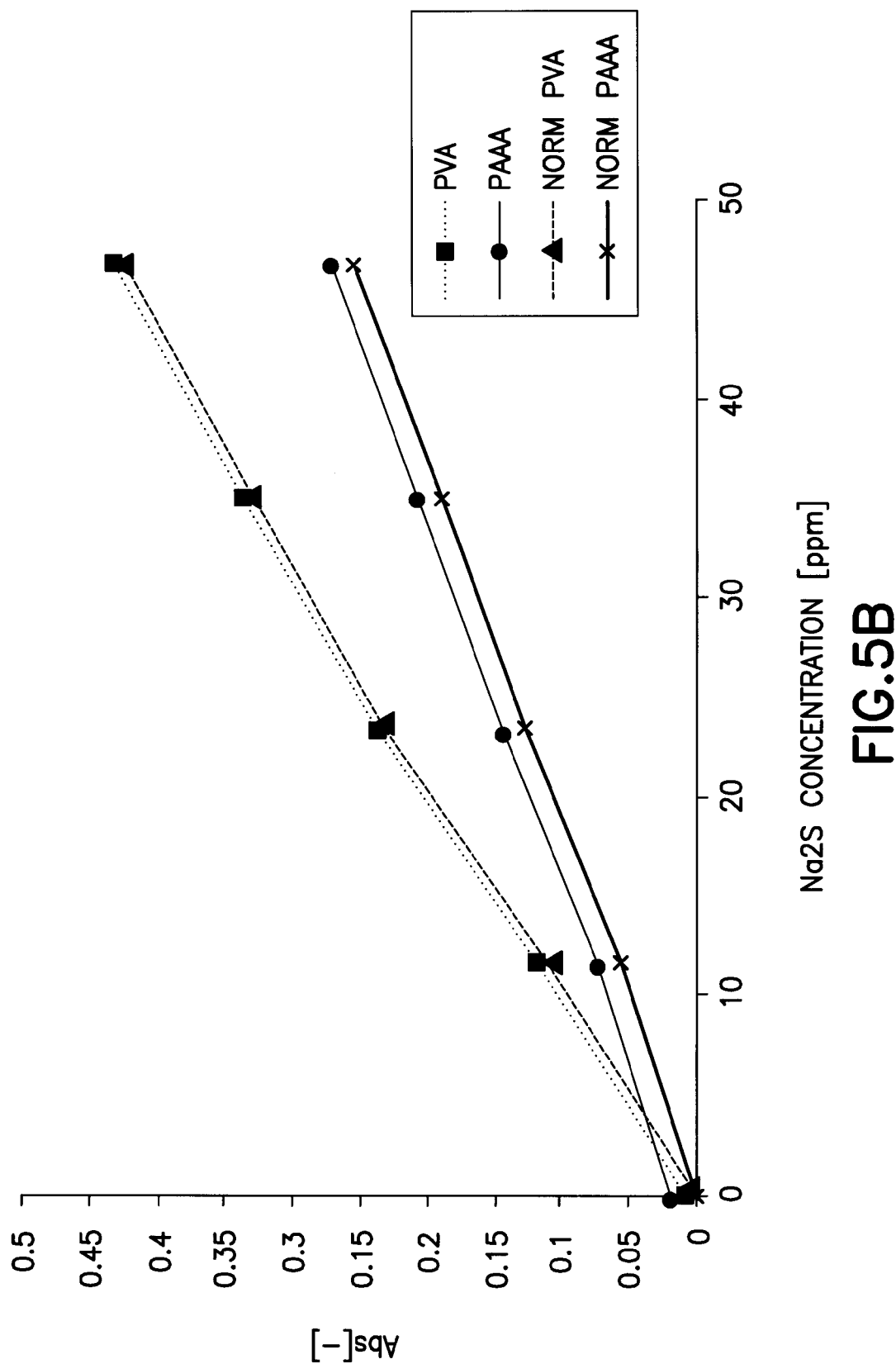
FIG. 5B shows the absorbance at 1000 nm of Cu ion solution reacted with sulfide heated at 100 deg C. for poly(vinyl alcohol) and poly (acrylic acid-co-acryl amide) as capping agents, according to embodiments of the disclosed subject matter.

Referring to FIGS. 5A and 5B, FIG. 5A shows the comparison of absorbance spectra of various amounts of sulfide added to Cu-PVA solution. In particular, FIG. 5A shows an increasing absorbance when sulfide concentration was increased during its addition to copper salt stabilized with poly(vinyl alcohol) (capping agent) in water, heated at 100 deg C. The color change versus concentration is shown in FIG. 5B together with results when copper salt is stabilized with poly (acrylic acid-co-acryl amide) (capping agent).

Figure 6:
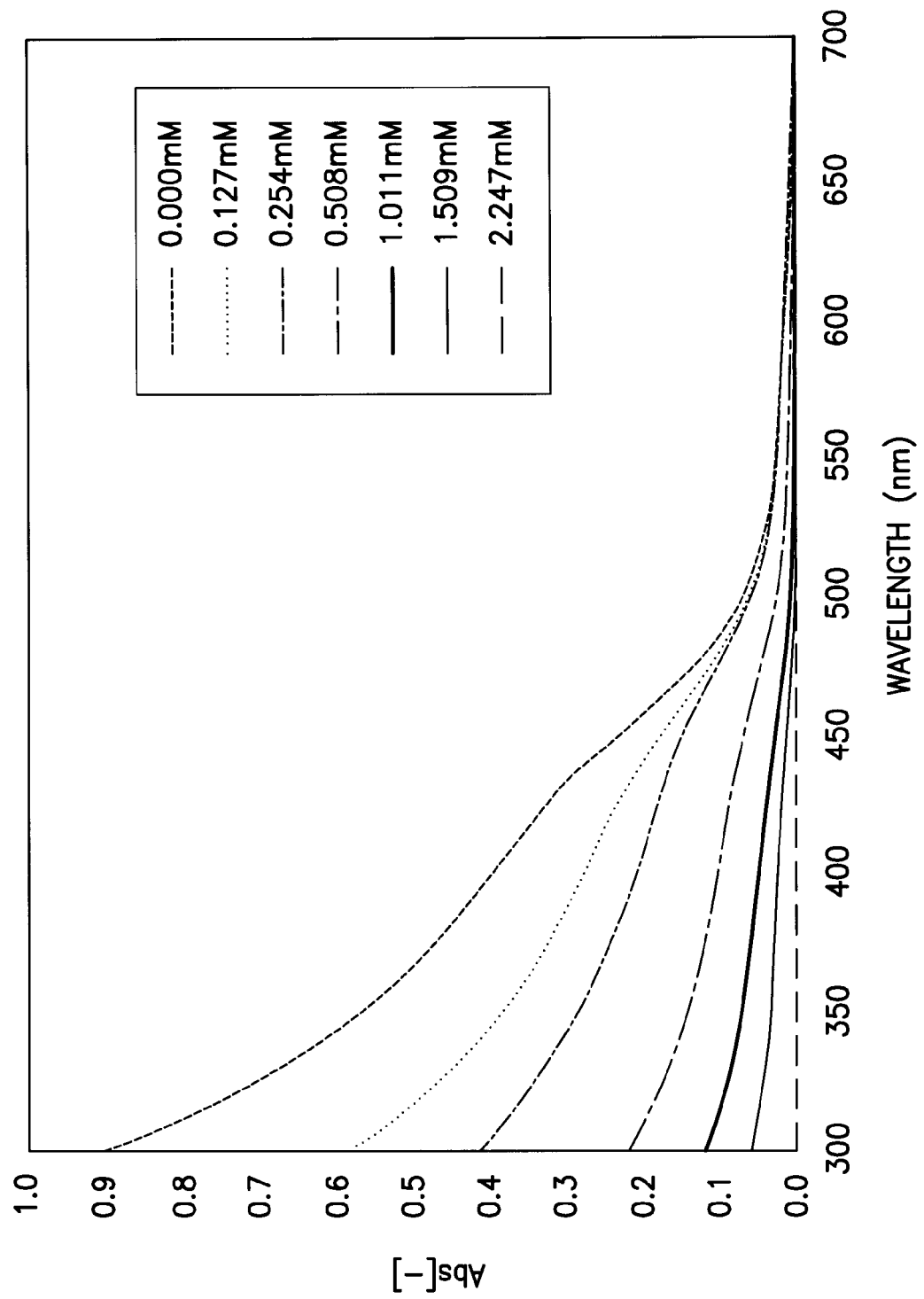
FIG. 6 shows the absorbance increase of Cd-PVP-Formamide solution added with various amounts of sodium sulfide, according to embodiments of the disclosed subject matter.

Referring to FIG. 6, FIG. 6 shows the absorbance increase of Cd-PVP-Formamide solution added with various amounts of sodium sulfide. In particular, FIG. 6 shows the UV-Vis result for cadmium based solution stabilized with poly(vinyl pyrrolidone) in formamide based solution stabilized with poly(acrylic acid) in water when sulfide was added in different concentrations.

Figure 7A:
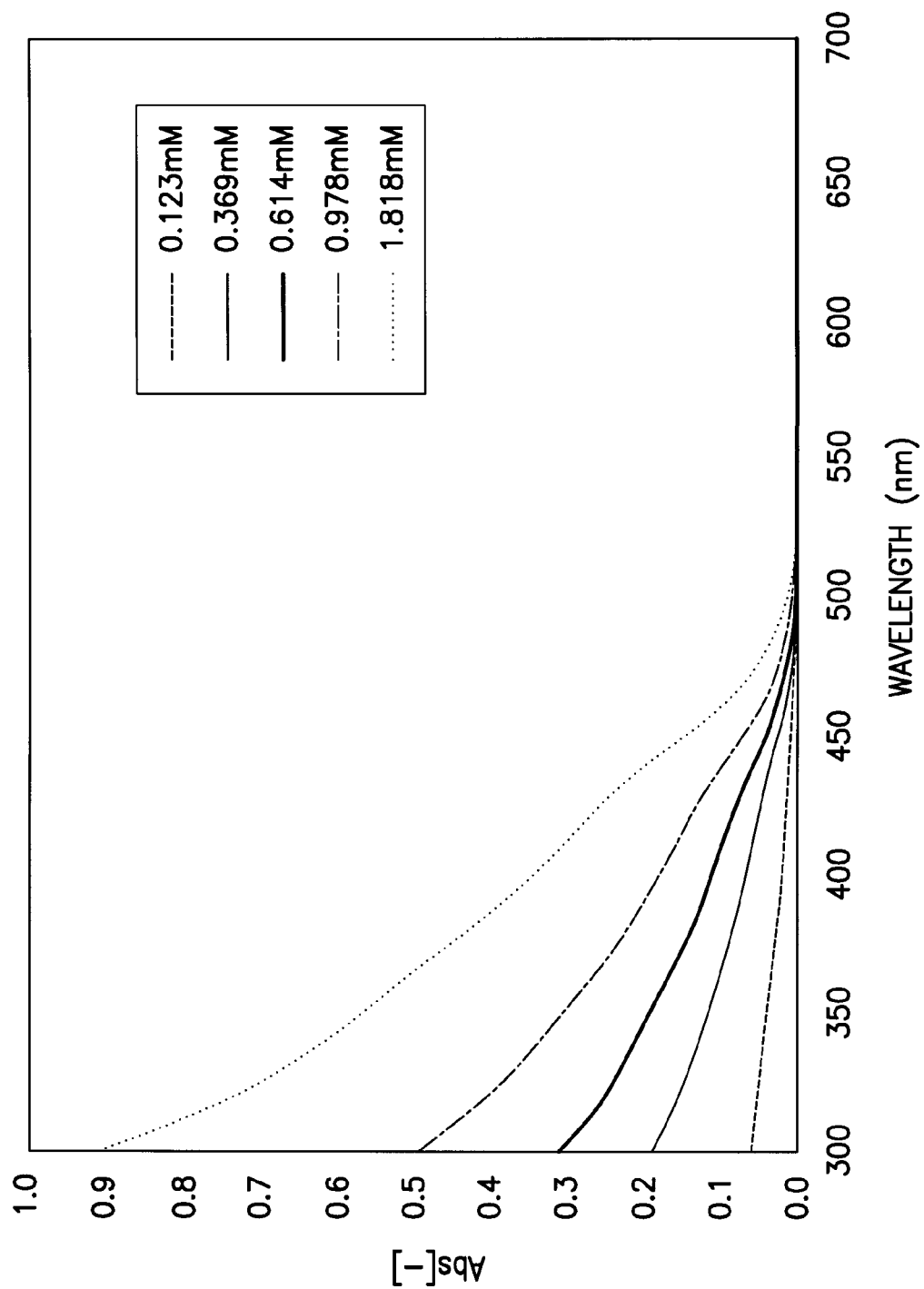
FIG. 7A shows the UV-Vis spectra of cadmium based solution with poly (acrylic acid) (PAA) in water after reaction with various amounts of sulfide, according to embodiments of the disclosed subject matter.
Figure 7B:
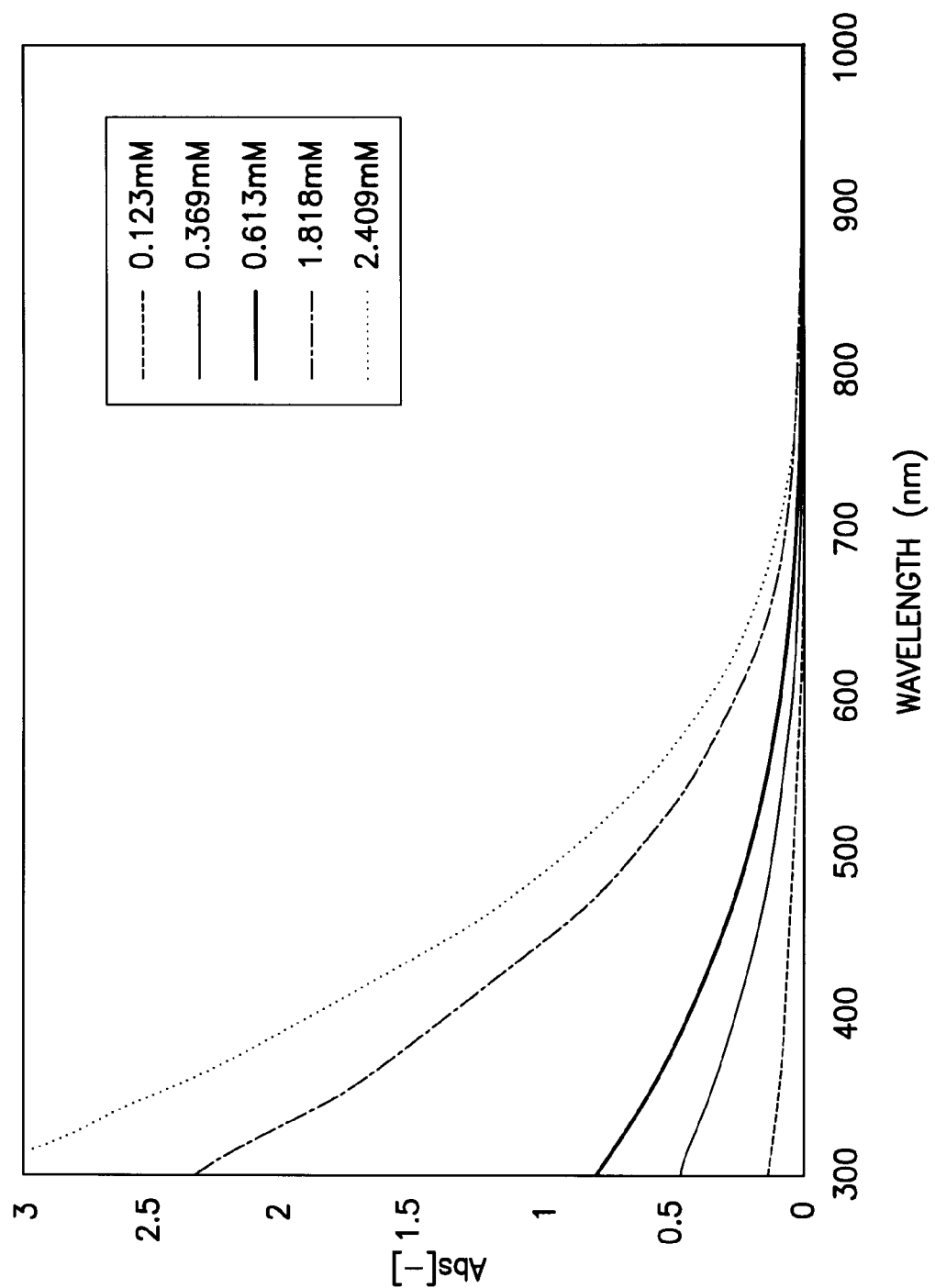
FIG. 7B shows the UV-Vis spectra of bismuth based solution with poly (acrylic acid) (PAA) in water after reaction with various amounts of sulfide, wherein FIG. 7A and FIG. 7B together provide for a comparison of the different shape profile of cadmium based solution and bismuth based solution, as well as noting that an absorption increase was not observed for bismuth based solution and cadmium based solution at wavelength>800 nm and 550 nm, respectively, according to embodiments of the disclosed subject matter.

Referring to FIGS. 7A and 7B, FIG. 7A shows the UV-Vis spectra of cadmium based solution with poly (acrylic acid) (PAA) in water after reaction with various amounts of sulfide. FIG. 7B shows the UV-Vis spectra of bismuth based solution with poly (acrylic acid) (PAA) in water after reaction with various amounts of sulfide. In viewing FIG. 7A and FIG. 7B together, it is noted it provides for a comparison of the different shape profile of cadmium based solution and bismuth based solution, as well as noting that an absorption increase was not observed for bismuth based solution and cadmium based solution at wavelength>800 nm and 550 nm, respectively.

Figure 8A:
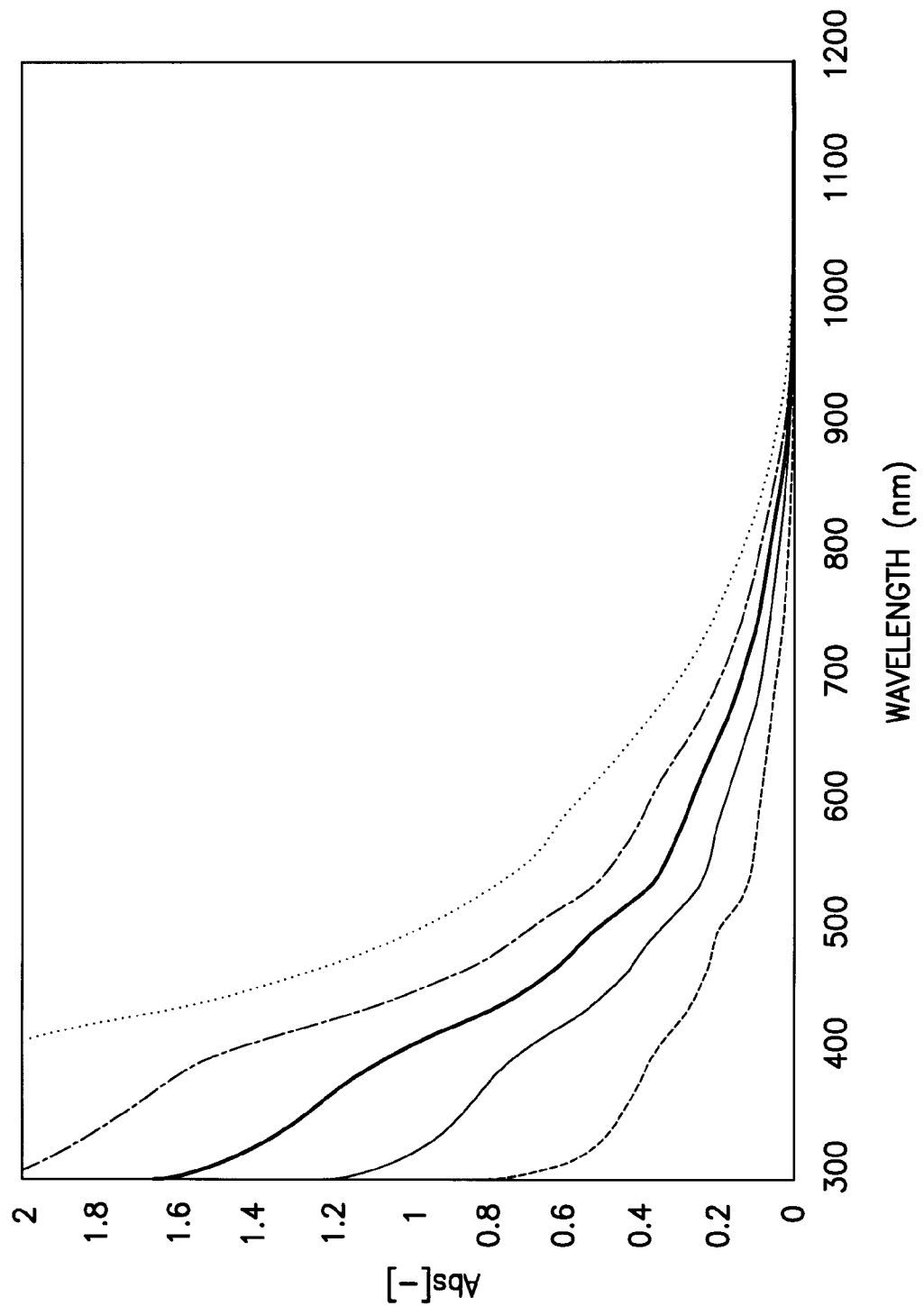
FIG. 8A shows the comparison of different shape profile of bismuth based solution stabilized with PVP in triethanolamine (TEA) after reaction with various amounts of sulfide at high temperature, according to embodiments of the disclosed subject matter.
Figure 8B:
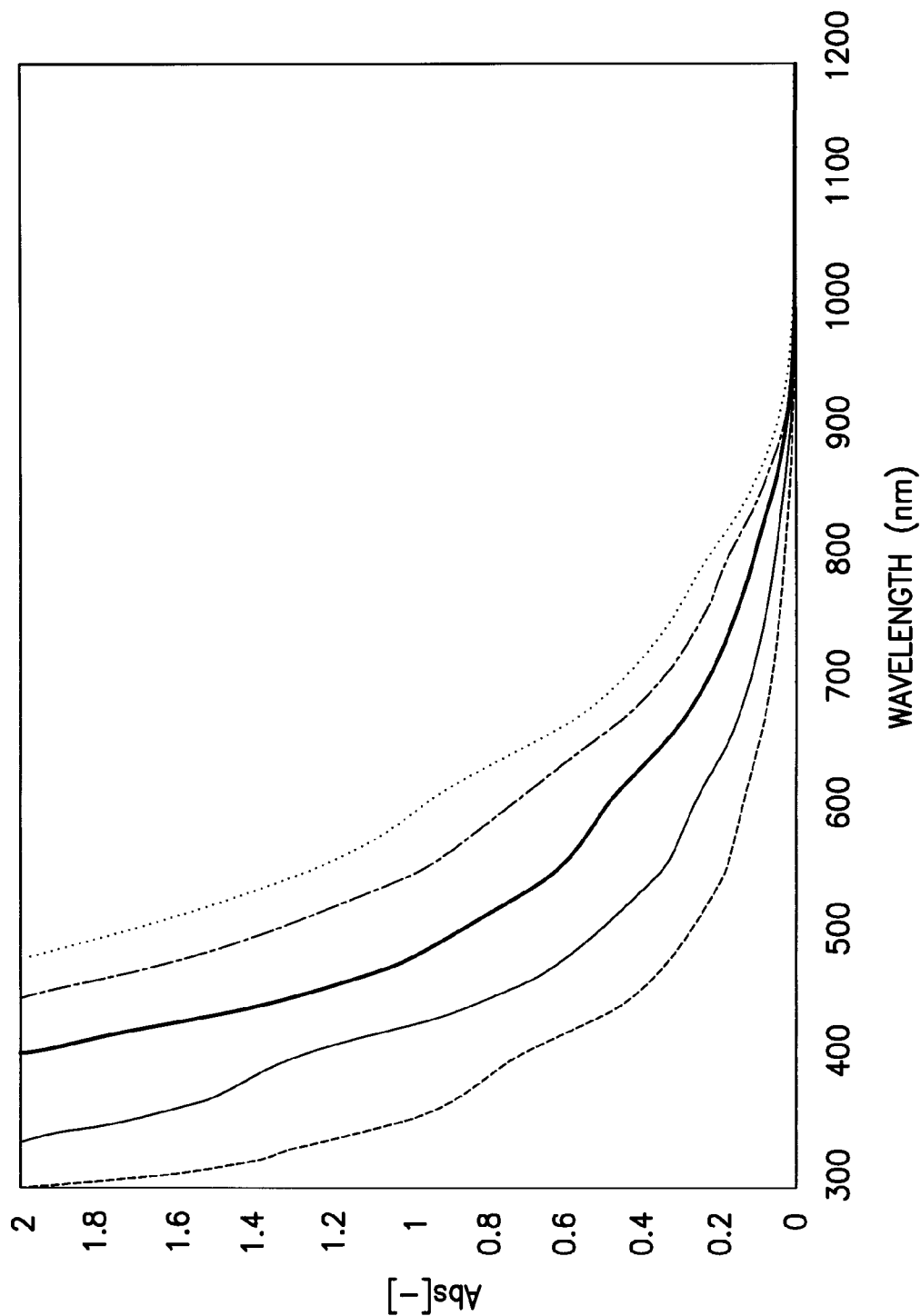
FIG. 8B shows the comparison of different shape profile of bismuth based solution stabilized with PVP in methyldiethanolamine (MDEA) after reaction with various amounts of sulfide at high temperature, according to embodiments of the disclosed subject matter.

While FIGS. 8A and 8B show the difference of high boiling point solvents to bismuth stabilized with poly (acrylic acid) based solutions at high temperature (150 deg C.). In particular, FIG. 8A shows the shape profile of bismuth based solution stabilized with PVP in triethanolamine (TEA) after reaction with various amounts of sulfide at high temperature. FIG. 8B shows the shape profile of bismuth based solution stabilized with PVP in methyldiethanolamine (MDEA) after reaction with various amounts of sulfide at high temperature.

Figure 9A:
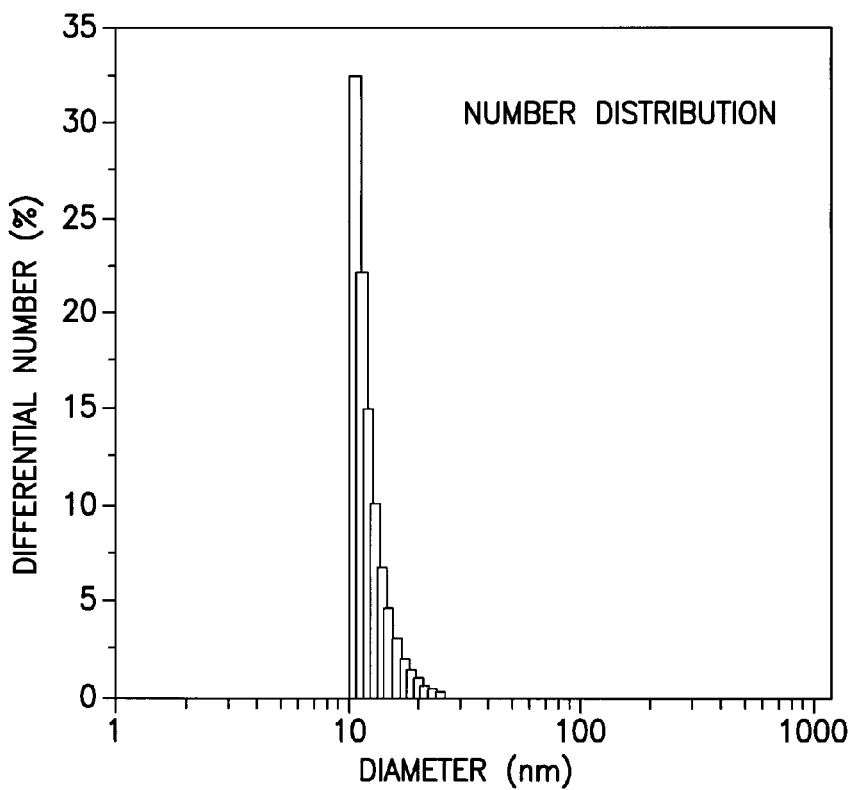
FIG. 9A shows the particle size distribution of bismuth sulfide ($Bi_2S_3$) nanocolloids stabilized with poly (acrylic acid) (PAA) as measured with the dynamic light scattering measurement, according to embodiments of the disclosed subject matter.
Figure 9B:
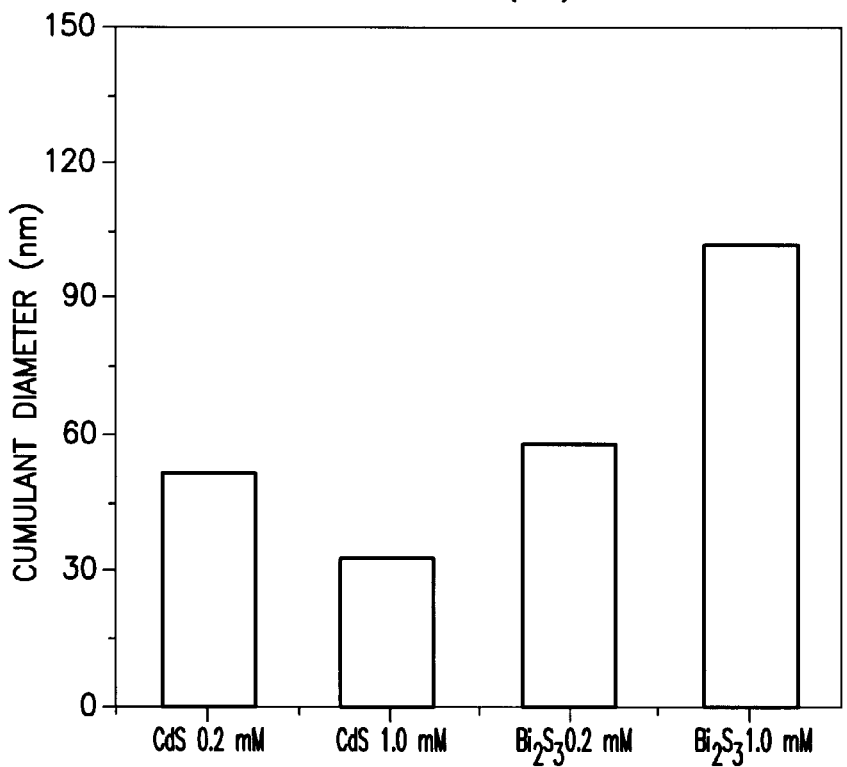
FIG. 9B shows the cumulant particle size for cadmium sulfide and bismuth sulfide ($Bi_2S_3$) at different concentrations as measured with the dynamic light scattering measurement, according to embodiments of the disclosed subject matter.
Figure 9C:
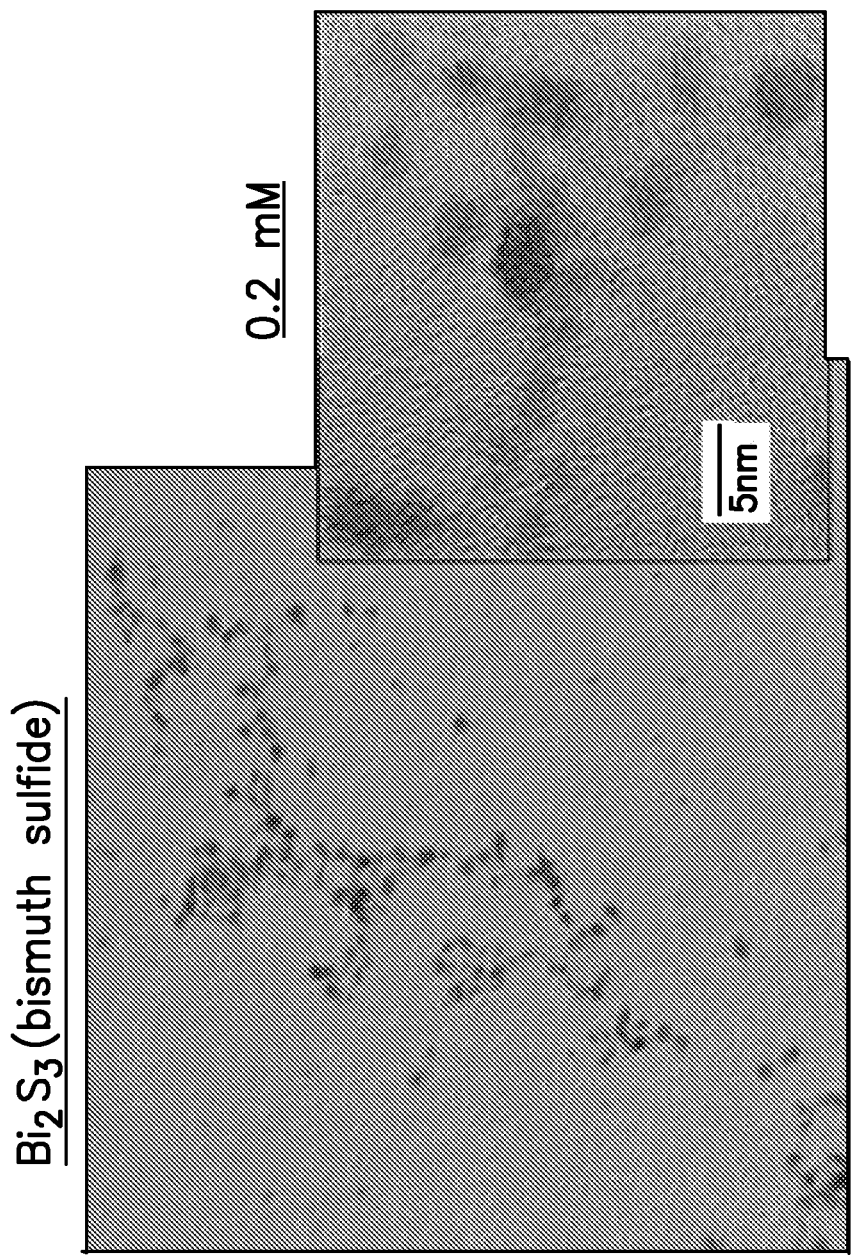
FIG. 9C illustrates TEM image of $Bi_2S_3$ nanoparticle stabilized with poly (acrylic acid) (PAA), according to embodiments of the disclosed subject matter.

FIGS. 9A, 9B and 9C show the characterization of bismuth sulfide and cadmium sulfide nanoparticles stabilized in poly (acrylic acid) (PAA) with dynamic light scattering and transmission electron microscopy. It is noted that the concentration difference did not affect particle size linearly. In particular, FIG. 9A shows the particle size distribution of bismuth sulfide ($Bi_2S_3$) nanocolloids stabilized with poly (acrylic acid) (PAA) as measured with the dynamic light scattering measurement. FIG. 9B shows the cumulant particle size for cadmium sulfide and bismuth sulfide ($Bi_2S_3$) at different concentrations as measured with the dynamic light scattering measurement. FIG. 9C illustrates the TEM image of ($Bi_2S_3$) nanoparticle stabilized with poly (acrylic acid) (PAA).

Figure 10A:
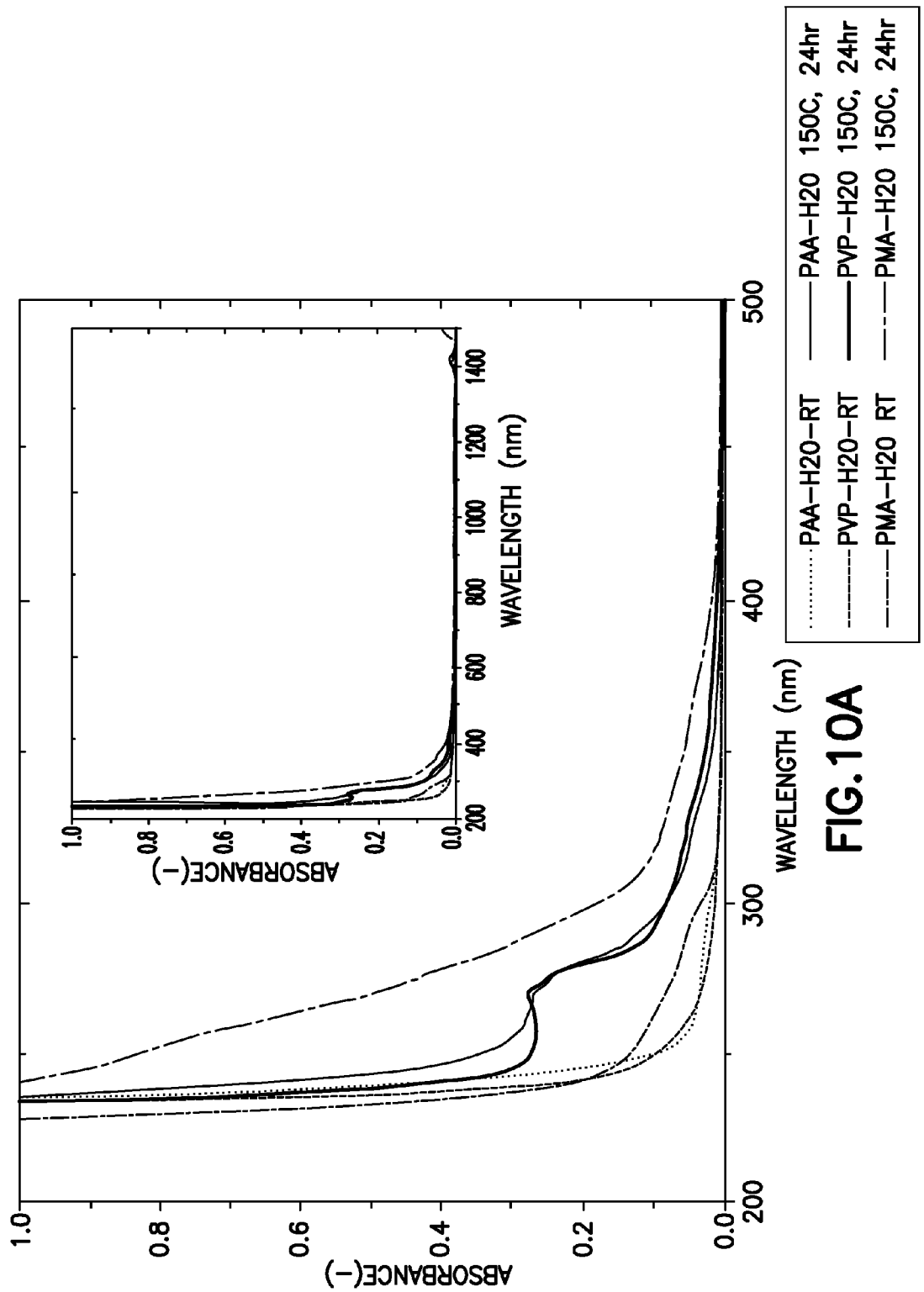
FIG. 10A shows the thermal stability test result of polymer solutions (poly (acrylic acid) (PAA), PVP and PMA), solutions were measured before and after heated at 150 deg C. for 24 hours, according to embodiments of the disclosed subject matter.
Figure 10B:
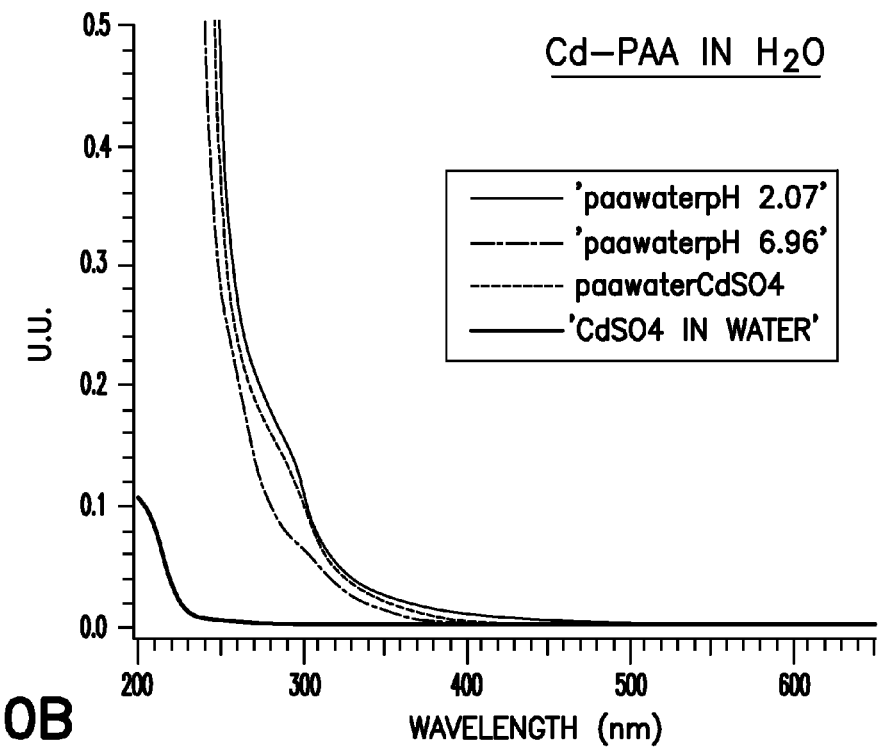
FIG. 10B shows the thermal stability test result of cadmium based solution stabilized with PAA, wherein measurements were conducted before and after these solutions were heated at 150 deg C. for 24 hours, according to embodiments of the disclosed subject matter.
Figure 10C:
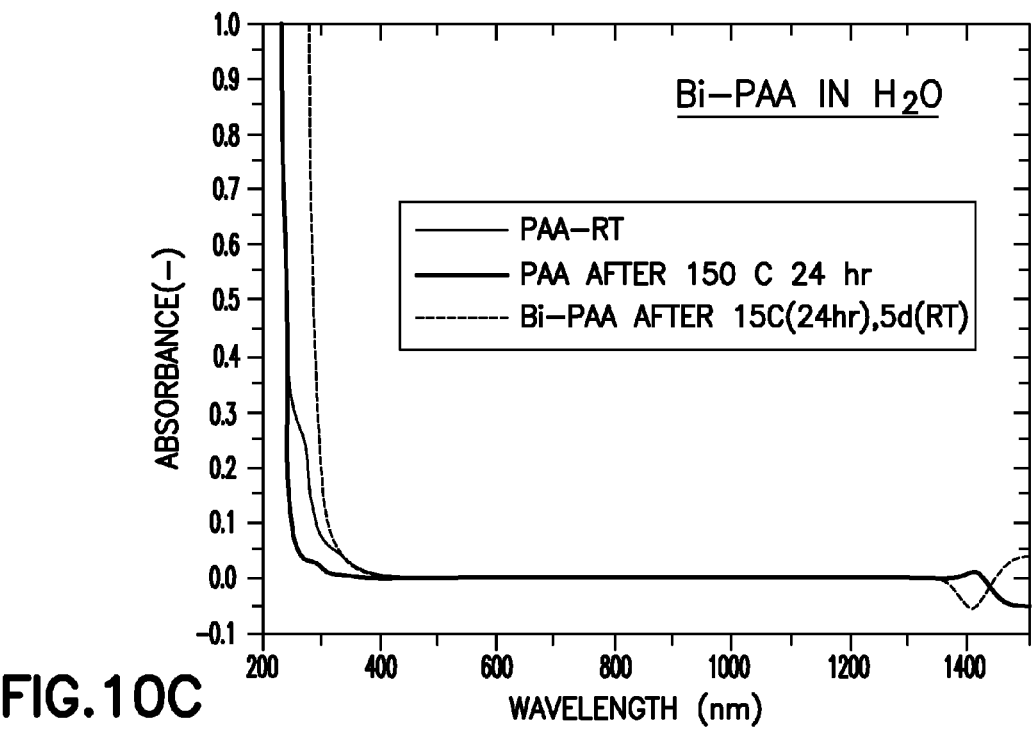
FIG. 10C shows the thermal stability test result of bismuth based solution stabilized with PAA, wherein measurements were conducted before and after these solutions were heated at 150 deg C. for 24 hours, according to embodiments of the disclosed subject matter.

FIGS. 10A, 10B and 10C proved the thermal stability of the reagents for downhole applications. In particular, FIG. 10A shows the thermal stability test result of polymer solutions (PAA, PVP and PMA), solutions were measured before and after heated at 150 deg C. for 24 hours. FIG. 10B shows the thermal stability test result of cadmium based solution stabilized with PAA, wherein measurements were conducted before and after these solutions were heated at 150 deg C. for 24 hours. FIG. 10C shows the thermal stability test result of bismuth based solution stabilized with PAA, wherein measurements were conducted before and after these solutions were heated at 150 deg C. for 24 hours.

Figure 11A:
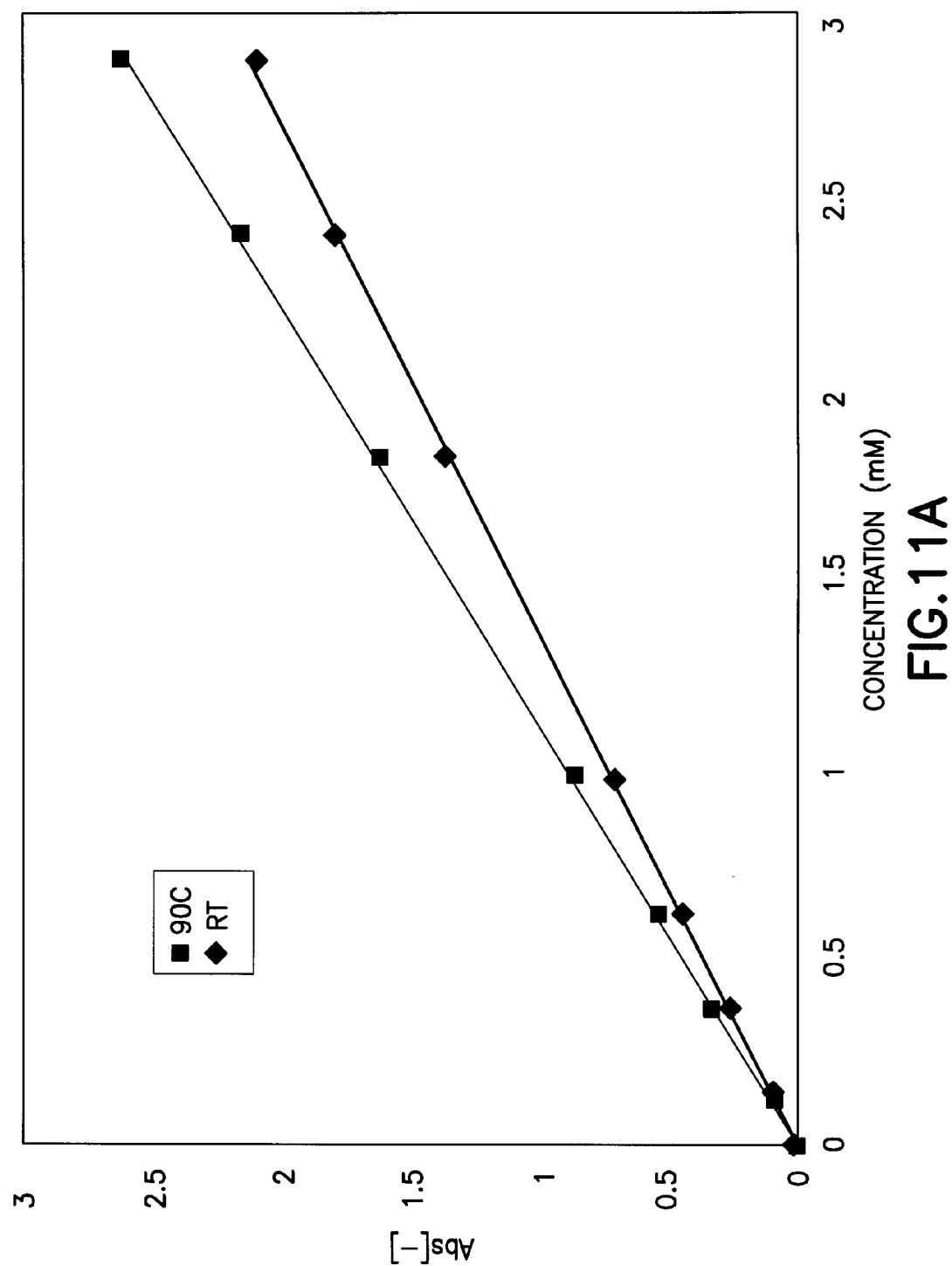
FIG. 11A shows the absorbance value at increasing sulfide addition for Bi-PAA-$H_2O$ before and pre-heated for 2 hours at 100 deg C., according to embodiments of the disclosed subject matter.
Figure 11B:
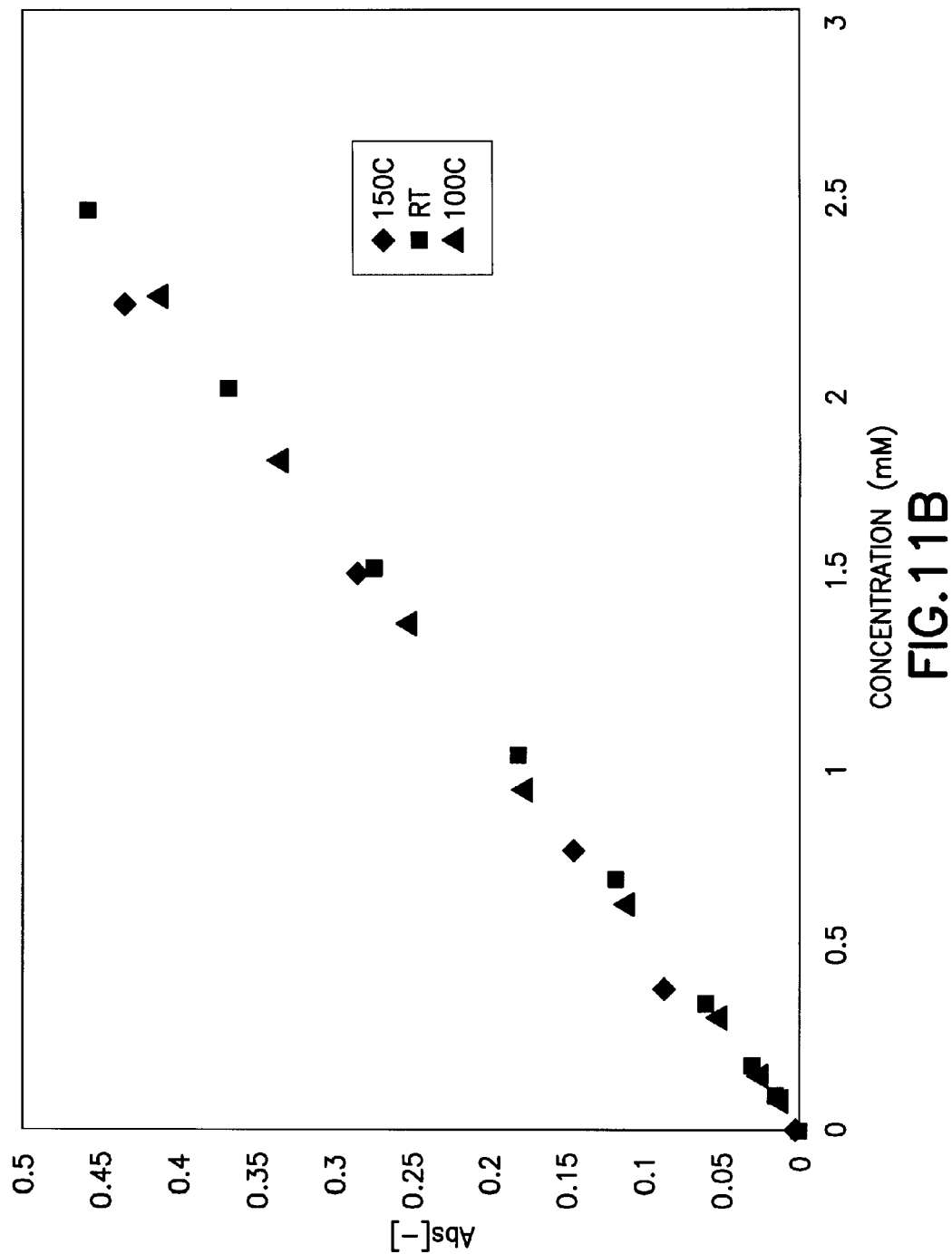
FIG. 11B shows the absorbance value at increasing sulfide addition for Cd-PAA-$H_2O$ before heated, pre-heated for 2 hours at 100 deg C. and 150 deg C., according to embodiments of the disclosed subject matter.

FIGS. 11A and 11B show the absorbance relation to sulfide concentration of bismuth in PAA and cadmium in PAA at room temperature, 100 deg C. (and preheated at 150 deg C. for cadmium based solution). In particular, FIG. 11A shows the absorbance value at increasing sulfide addition for Bi-PAA-$H_2O$ without heating and heated for 2 hours at 100 deg C. FIG. 11B shows the absorbance value at increasing sulfide addition for Cd-PAA-$H_2O$ before heating, heated for 2 hours at 100 deg C. and 150 deg C.

Figure 12A:
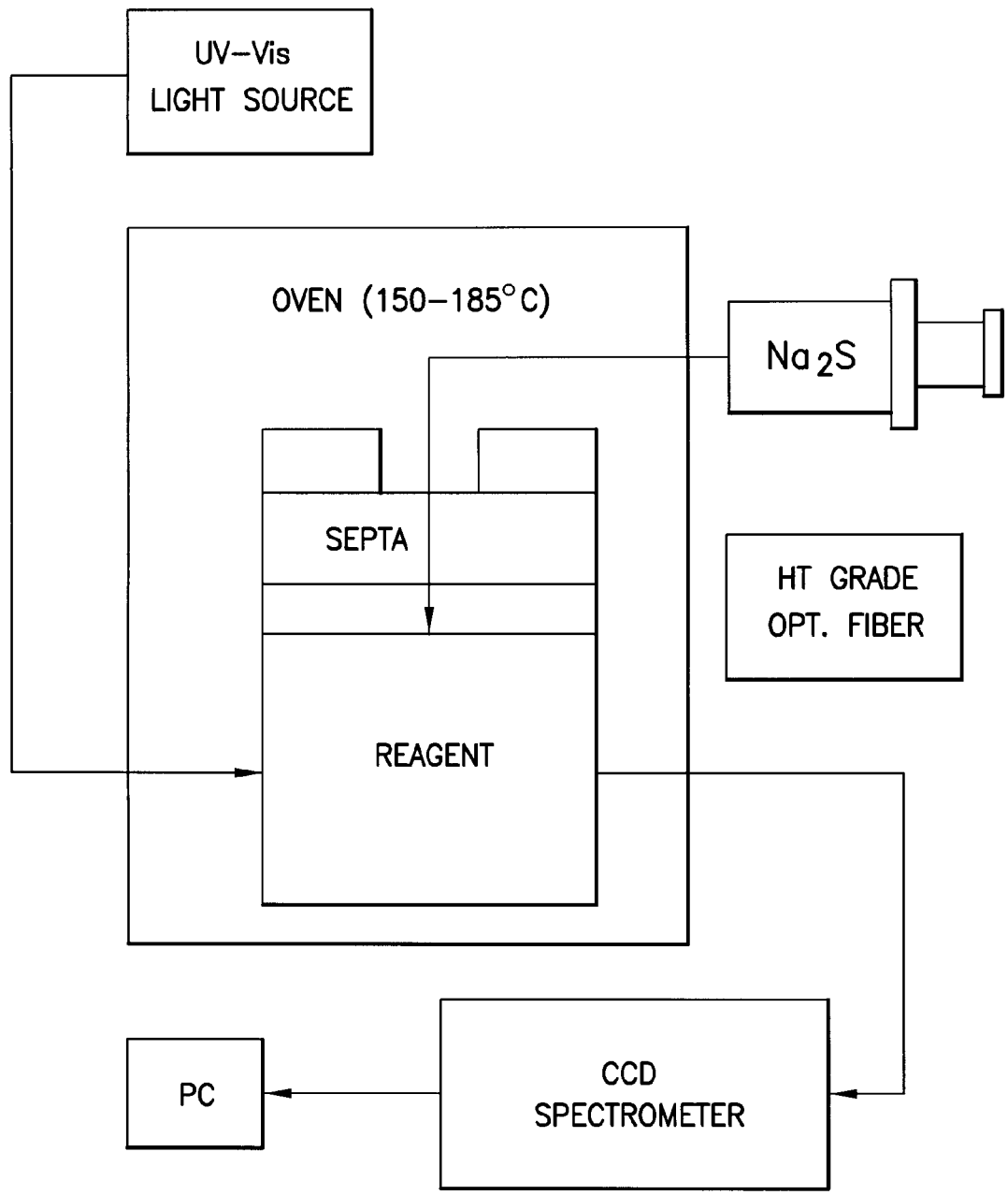
FIG. 12A illustrates the experimental setup for sulfide injection at high temperature, according to embodiments of the disclosed subject matter.
Figure 12B:
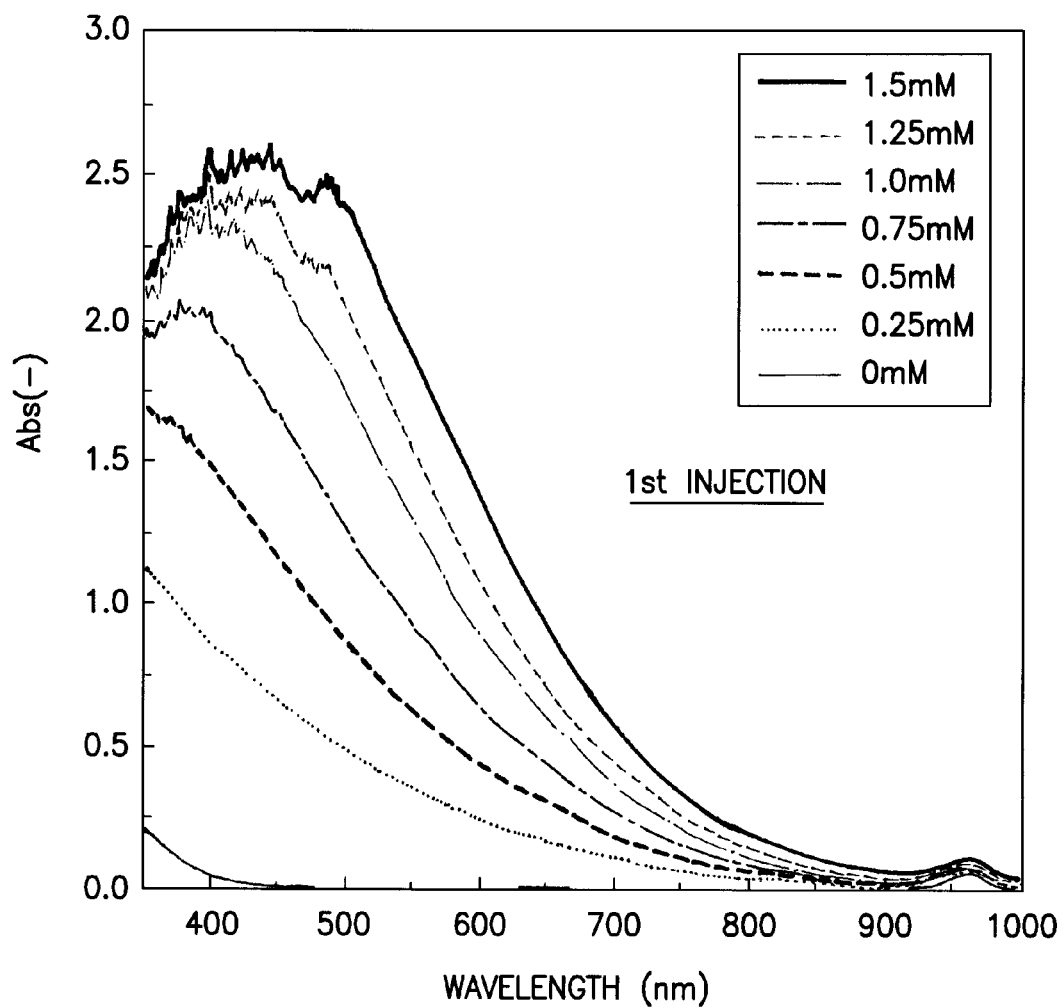
FIG. 12B shows the UV-Vis spectra showing absorbance increase when sulfide was injected incrementally to Bi-PAA-$H_2O$ solution at 150 deg C., according to embodiments of the disclosed subject matter.

FIG. 12A illustrates the experimental setup for sulfide injection at high temperature. FIG. 12B shows the UV-Vis spectra showing absorbance increase when sulfide was first injected incrementally to Bi-PAA-$H_2O$ solution at 150 deg C.

Further, while the present disclosed subject matter has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present disclosed subject matter in its aspects. Although the present disclosed subject matter has been described herein with reference to particular means, materials and embodiments, the present disclosed subject matter is not intended to be limited to the particulars disclosed herein; rather, the present disclosed subject matter extends to all functionally equivalent structures, methods and uses, such as are within the scope of the appended claims.

What is claimed is:

1. A reagent mixture for spectroscopic detection of hydrogen sulfide within formation fluid, the reagent mixture comprising:
   a solvent;
   metal ions dissolved in the solvent for reacting with hydrogen sulfide thereby forming an insoluble metal sulfide species, the metal ions selected from the group consisting of bismuth and cadmium; and
   a capping agent that limits growth of the insoluble metal sulfide species by steric stabilization under downhole conditions to prevent precipitation and to provide for spectroscopic detection of the insoluble metal sulfide species stabilized within the mixture,
   wherein the capping agent is comprised of a soluble polymer from the group consisting of one of a poly(acrylamide-co-acrylic acid), a poly(acrylic acid), a chitosan, a poly(vinyl pyridine), a poly(ethylene glycol) monolaurate, a poly(ethylene oxide), a poly(vinyl alcohol), a poly(4-styrene sulfonic acid), a poly (methacrylic acid), and a poly (vinyl pyrrolidone).

2. The reagent mixture according to claim 1, wherein the solvent is one of water, an organic polar solvent, an ionic liquid, or some combination thereof.

3. The reagent mixture according to claim 1, wherein the capping agent is a soluble polymer that provides for spectroscopic detection of the metal sulfide species under downhole conditions of temperatures greater than 100 degrees Celsius.

4. The reagent mixture according to claim 1, wherein the capping agent has an approximate concentration of less than 5 mass percent.

5. The reagent mixture according to claim 1, further comprising a chelating ligand to sustain endurance at high temperatures under downhole conditions.

6. The reagent mixture according to claim 5, wherein the chelating ligand has at least one pK lower than a pH of the reagent mixture.

7. The reagent mixture according to claim 5, wherein a ratio of the chelating ligand to the metal ion is less than 2%.

8. The reagent mixture according to claim 1, wherein the reagent mixture changes at least one optical property of the formation fluid when the reagent mixture is mixed with the formation fluid.

9. A reagent mixture for spectroscopic detection of hydrogen sulfide within formation fluid, the reagent mixture comprising:
   a solvent;
   metal ions dissolved in the solvent for reacting with hydrogen sulfide thereby forming an insoluble metal sulfide species, the metal ions selected from the group consisting of bismuth and cadmium;
   a capping agent that limits growth of the insoluble metal sulfide species by steric stabilization under downhole conditions to prevent precipitation and to provide for spectroscopic detection of the insoluble metal sulfide species stabilized within the mixture, and
   a radical scavenging agent to reduce a rate of degradation of the metal sulfide species produced by the metal ions.

10. The reagent mixture according to claim 9, wherein the radical scavenging agent is less than 5 volume percent.

11. The reagent mixture according to claim 1, wherein the steric stabilization includes an electro-steric stabilization.

12. The mixture according to claim 1, wherein the downhole conditions comprise temperatures greater than 100 degrees Celsius.

13. A homogenous reagent mixture for spectroscopic detection of hydrogen sulfide in formation fluid, the homogenous reagent mixture comprising:
   a solvent;
   metal ions dissolved in the solvent for reacting with hydrogen sulfide thereby forming an insoluble metal sulfide species, the metal ions selected from the group consisting of bismuth and cadmium; and
   a capping agent that limits growth of the insoluble metal sulfide species by steric stabilization under downhole conditions to prevent precipitation and to provide for spectroscopic detection of the insoluble metal sulfide species stabilized within the mixture,
   wherein the pH range of the homogenous reagent mixture is between 2 and 5.

14. The homogenous reagent mixture according to claim 13, further comprising a radical scavenging agent to reduce a rate of degradation of the bismuth sulfide species produced by the bismuth metal ions.

15. The homogenous reagent mixture according to claim 13, further comprising a chelating ligand having at least one pK lower than the pH of the reagent mixture.

16. The homogeneous reagent-mixture according to claim 13, wherein the steric stabilization includes an electro-steric stabilization.

17. A method of detecting hydrogen sulfide in a fluid, the method comprising:
combining a reagent mixture with the fluid to form a solution, wherein the reagent mixture includes:
a solvent
metal ions dissolved in the solvent for reacting with hydrogen sulfide to form an insoluble metal sulfide species, and
a capping agent that limits growth of the insoluble metal sulfide species by steric stabilization under downhole conditions to prevent precipitation and to provide for spectroscopic detection of the insoluble metal sulfide species; and
spectroscopically interrogating the combined reagent mixture and the fluid to detect the presence of hydrogen sulfide in the fluid using an optical property of the insoluble metal sulfide species stabilized within the solution.

18. The method according to claim 17, wherein the optical property includes one of an optical density of the metal sulfide species or a fluorescence of the metal sulfide species.

19. The method according to claim 17, further comprising:
spectroscopically interrogating at least one of the fluid or the reagent mixture before the combining.

20. The method according to claim 17, further comprising a radical scavenging agent to reduce a rate of degradation of the bismuth sulfide species.

21. The method according to claim 17, wherein the fluid is a formation fluid.

22. The method according to claim 21, wherein the combining further comprises introducing the reagent mixture into a downhole flowline containing the formation fluid and the spectroscopically interrogating further comprises interrogating through an optical window in the flowline downstream from the location of introduction of the reagent mixture.

23. The method according to claim 21, wherein the combining further comprises introducing the formation fluid into a container containing the reagent mixture and the interrogating further comprises interrogating through an optical window in a wall of the container while in a subterranean environment.

24. The method according to claim 23, wherein the combining further comprises mechanically stirring the reagent mixture and the formation fluid in the container to shorten a rate of time used to carry out the interrogating.

25. The method according to claim 21, wherein the combining further comprises introducing the formation fluid into a container containing the reagent mixture, introducing the combined homogenous reagent mixture and the formation fluid from the container into a downhole flowline, and spectroscopically interrogating through an optical window in a wall of the flowline.

26. The method according to claim 21, further comprising adding chelating ligands to the reagent mixture.

27. The method according to claim 17, wherein the steric stabilization includes an electro-steric stabilization.

28. The method according to claim 17, wherein the downhole conditions comprise temperatures greater than 100 degrees Celsius.

29. A method of detecting hydrogen sulfide in a formation fluid using a downhole tool, the method comprising:
exposing a reagent mixture with the formation fluid to form a solution using the downhole tool, wherein the reagent mixture includes:
a solvent;
metal ions dissolved in the solvent for reacting with hydrogen sulfide to form a metal sulfide species, and
a capping agent that limits growth of the insoluble metal sulfide species by steric stabilization to provide for spectroscopic detection of the metal sulfide species;
spectroscopically interrogating the exposed reagent mixture using the downhole tool to detect the presence of hydrogen sulfide in the fluid using an optical property of the metal sulfide species stabilized within the solution.

30. A system for detecting hydrogen sulfide, the system comprising:
a reagent mixture for combining with a fluid to form a solution, the reagent mixture comprising:
a solvent;
metal ions dissolved in the solvent for reacting with hydrogen sulfide to form a metal sulfide species, and
a capping agent that limits growth of the insoluble metal sulfide species by steric stabilization under downhole conditions to prevent precipitation and to allow for spectroscopic detection of the metal sulfide species stabilized within the solution;
a reagent mixture delivery system for exposing the reagent mixture to the fluid; and
an optical detection system for interrogating the exposed reagent mixture to determine the presence of hydrogen sulfide within the fluid.

31. A system according to claim 30, wherein the optical detection system uses spectroscopy detection to detect at least one optical property of the exposed reagent mixture.

32. The system according to claim 30, wherein the reagent mixture delivery system is a downhole reagent mixture delivery system that includes a mixture reservoir and a valve system for introducing the reagent mixture into a flowline for carrying the fluid, and the optical detection system includes a light source, an interrogation window in the flowline, and an optical detector.

33. The system according to claim 30, wherein the steric stabilization includes an electro-steric stabilization.

* * * * *